United States Patent
Katayev et al.

(10) Patent No.: US 11,655,203 B2
(45) Date of Patent: May 23, 2023

(54) NITRATION

(71) Applicant: ETH ZURICH, Zürich (CH)

(72) Inventors: Dmitry Katayev, Zürich (CH); Kun Zhang, Zürich (CH); Roxan Calvo, Zürich (CH)

(73) Assignee: ETH ZURICH, Zürich (CH)

( * ) Notice: Subject to any disclaimer, the term of this patent is extended or adjusted under 35 U.S.C. 154(b) by 0 days.

(21) Appl. No.: 17/288,819

(22) PCT Filed: Oct. 24, 2019

(86) PCT No.: PCT/EP2019/079108
§ 371 (c)(1),
(2) Date: Apr. 26, 2021

(87) PCT Pub. No.: WO2020/084094
PCT Pub. Date: Apr. 30, 2020

(65) Prior Publication Data
US 2022/0009875 A1 Jan. 13, 2022

(30) Foreign Application Priority Data

Oct. 26, 2018 (EP) ...................... 8202956

(51) Int. Cl.
*C07C 201/08* (2006.01)
*C07D 275/06* (2006.01)

(52) U.S. Cl.
CPC .......... *C07C 201/08* (2013.01); *C07D 275/06* (2013.01)

(58) Field of Classification Search
CPC .............. C07C 201/08; C07C 2601/02; C07C 2601/14; C07C 2602/08; C07C 2603/24; C07C 2603/84; C07C 209/02; C07C 231/12; C07C 253/30; C07C 315/04; C07C 319/20; C07D 275/06; C07D 209/02; C07D 233/76; C07D 213/61; C07D 207/40; C07D 209/48; C07D 231/14; C07D 233/92; C07D 239/30; C07D 307/71; C07D 311/72; C07D 333/12; C07J 41/005
USPC .......................................... 549/210; 548/210
See application file for complete search history.

(56) References Cited

U.S. PATENT DOCUMENTS

| 5,946,638 | A | 8/1999 | Jayasuriya et al. | |
| 6,468,487 | B1 | 10/2002 | Ishii et al. | |
| 2022/0009895 | A1* | 1/2022 | Katayev | C07D 275/06 |

OTHER PUBLICATIONS

Yan et al; "Recent advances in the synthesis of aromatic nitro compounds;" Organic & Biomolecular Chemistry; 2013; pp. 2554-2566; vol. 11, No. 16.
Kozlova et al.; "Chemistry of Nitro Imides;" Bulletin of the Academy of Sciences of the USSR Division of Chemical Science; 1982; pp. 1712-1714.
Zhang et al.; "N-Trifluoromethylthio-dibenzenesulfonimide: A Shelf-Stable, Broadly Applicable Electrophilic Trifluoromethlythiolating Reagent;" The Journal of Organic Chemistry; 2016; pp. 7486-7509; vol. 81.
Klumpp; "Chapter 1: Electrophilic Aromatic Substitution: Mechanism;" Arene Chemistry: Reaction Mechanisms and Methods for Aromatic Compounds; 2016; pp. 3-31; John Wiley and Sons.
Brinck et al.; "Chapter 4: The Use of Quantum Chemistry for Mechanistic Analyses of SEAr Reactions;" Arene Chemistry: Reaction Mechanisms and Methods for Aromatic Compounds; 2016; pp. 83-105; John Wiley and Sons.
Nalbandian et al.; "Lewis Base/Bronsted Acid Dual-Catalytic C—H Sulfenylation of Aromatics;" Org. Lett.; 2018; pp. 3211-3214; vol. 20.
Xu et al.; "N-Trifluoromethylthiosaccharin: An Easily Accessible, Shelf-Stable, Broadly Applicable Trifluoromethylthiolating Reagent;" Angew. Chem. Int. Ed.; 2014; pp. 9316-9320; vol. 53.
Dec. 5, 2019 Search Report issued in International Patent Application No. PCT/EP2019/079108.
Dec. 5, 2019 Written Opinion issued in International Patent Application No. PCT/EP2019/079108.

* cited by examiner

*Primary Examiner* — Taylor V Oh
(74) *Attorney, Agent, or Firm* — Oliff PLC

(57) ABSTRACT

A process for preparing a nitrated compound, including the step of reacting a compound (A) including at least one substituted or unsubstituted aromatic or heteroaromatic ring, wherein the heteroaromatic ring includes at least one heteroatom selected from the group consisting of oxygen, sulfur, phosphor, selenium and nitrogen, with a compound of formula (I)

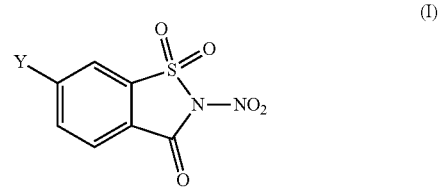

wherein Y is selected from the group consisting of hydrogen and nitro.

18 Claims, 2 Drawing Sheets

NITRATION

The invention relates to a process for preparing a nitrated compound.

Nitroarenes continue to be in high demand for the synthesis of pharmaceuticals, agricultural chemicals, dyes, solvents, materials and energetic compounds both in academia and industry. Even today, nitroarenes and nitroheteroarenes are almost exclusively synthesized by electrophilic nitration of arenes, respectively heteroarenes, with excess of nitric acid or mixed strong-acid systems, such as $H_2SO_4/HNO_3$ at temperatures up to 135° C. Such acidic reaction conditions represent a limitation in terms of tolerance towards acid-sensitive and/or heat-sensitive functional groups and result in a selectivity problem leading to the formation of a complex mixture of regioisomers and over-nitrated side products.

Despite the hazardous and environmentally unfriendly reputation of such processes, the use of $H_2SO_4/HNO_3$ has been retained over the years as a fundamental industrial approach for the preparation of nitroarenes and nitroheteroarenes in a large scale.

Modern, regiospecific synthesis of nitroarenes includes the ipso-nitration reaction of aryl halides, pseudo halides, organometallic compound, or carboxylates using metal nitrate salts as the $NO_2$ source (e.g. $AgNO_3$, $Bi(NO_3)\times6H_2O$, $Fe(NO_3)_3\times9H_2O$, $Ca(NO_2)_2$) and Pd, Rh or Cu catalysts. Most commonly, these methodologies do not require the use of acidic reaction conditions. However, these reagents are often expensive or difficult to prepare, and the methods can be applied only for a specific class of arenes and have been performed on a small scale.

Alternatively, nitroarenes can be prepared via oxidation process of the corresponding primary aryl amines. However, it requires additional chemical steps and the reaction conditions often do not tolerate various functional groups.

From up-scale standpoint, all above mentioned methodologies suffer from practical drawbacks, such as the use of toxic and high cost reagents, the use of specific technical equipment, difficulties in work-up procedures to isolate desired products and the formation of overstoichiometric amounts of acidic or metal waste, the disposal of which is often problematic.

Yan et al, «Recent advances in the synthesis of aromatic nitro compounds», Org. Biomol. Chem., 2013, 11, 2554-2566, discuss in detail different approaches to get nitroarenes and nitroheteroarenes.

U.S. Pat. No. 6,468,487 discloses a catalyst useful for nitrating a substrate. In addition, U.S. Pat. No. 5,946,638 discloses a method for the nitration of substituted aromatic compounds having at least one ring activating ortho, and para directing substituent group. The process comprises the steps of heating said aromatic compound in the presence of a solid acidic small pore size zeolite catalyst at a temperature within the range of 70-90° C., and adding concentrated nitric acid having a concentration ranging from 90-98% to the heated mixture, so resulting in a product having a high proportion of para and ortho nitro isomers.

Thus, the application of the above approaches is limited, especially for the drug discovery via late-stage functionalization of complex molecules.

The problem of the present invention is therefore to provide a more general, inexpensive, practical, safe, and green process for the nitration of compounds comprising at least one aromatic or heteroaromatic ring.

The problem is solved by the process according to claim 1. Further preferred embodiments are subject of the dependent claims.

Surprisingly, it was found that the process according to the present invention allows to nitrate with excellent chemical efficiency arene compounds comprising at least one substituted or unsubstituted aromatic or heteroaromatic ring. The nitrating agent according to the present invention has an outstanding reactivity and can be used to nitrate a variety of compounds comprising an aromatic or heteroaromatic ring under mild reaction conditions with yields in the range of 60 to 100%, preferably 80 to 100%. In particular, the process according to the present invention allows a rapid and highly efficient incorporation of the $NO_2$ group into organic molecules of different sizes and complexity. Moreover, the process of the present invention allows to carry out a green and safe mono-nitration of the starting material avoiding over-nitration and the formation of unwanted oxidized by-products, which are often difficult to separate from the desired product. In addition, the process according to the present invention generates as side product the saccharin or saccharin derivative which can be recovered and further re-used in the synthesis of the nitration reagent.

Figure 1:
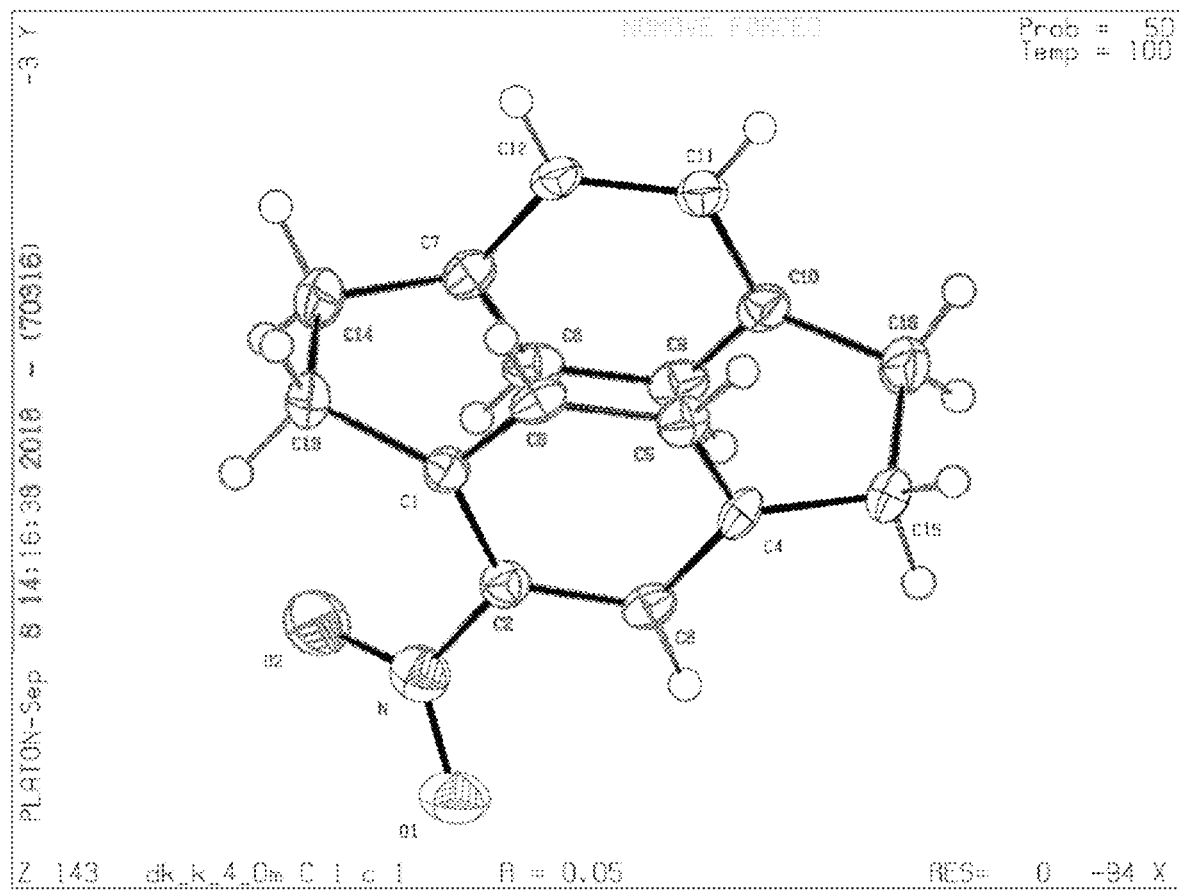
FIG. 1 shows the crystal structure of an exemplary compound.

Compound (A) is the starting material of the process according to the present invention and comprises at least one substituted or unsubstituted aromatic or heteroaromatic ring, wherein said heteroaromatic ring comprises at least one heteroatom selected from the group consisting of oxygen, sulfur, phosphor, selenium and nitrogen. The process according to the present invention involves the reaction step wherein compound (A) is reacted with a compound of formula (I).

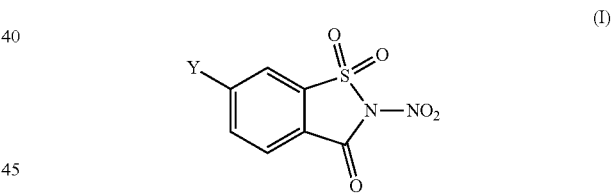

(I)

wherein Y is selected from the group consisting of hydrogen and nitro.

Compound (A) of the process according to the present invention comprises at least one substituted or unsubstituted aromatic or heteroaromatic ring, wherein said heteroaromatic ring comprises at least one heteroatom selected from the group consisting of oxygen, sulfur, phosphor, selenium and nitrogen. Compound (A) comprises the at least one substituted or unsubstituted ring as structural part of a bigger complex molecule or it only consists of said at least one unsubstituted or substituted aromatic ring. Thus, the expression "compound (A)" encompasses arenes and heteroarenes as well as compounds comprising one or more aromatic or heteroaromatic rings in their chemical structure, such as for example estrone, estradiol and estriol. If more than one aromatic or heteroaromatic ring is present, said rings may be fused together or being connected through a bond such as an alkylene group or the like with each other. In other words, compound (A) can be a small, medium or large organic compound comprising or consisting of a substituted or unsubstituted aromatic or heteroaromatic ring. Compound (A) can even be a complex molecule optionally bearing diverse functionalities such as steroid derivatives, ibuprofen derivatives and delamanid derivatives.

The regioselectivity of the nitration reaction may be predicted by the skilled person. (see for example Douglas A. Klumpp; Arene Chemistry: Reaction Mechanisms and Methods for Aromatic Compounds, 2016, (John Wiley and Sons, Inc) and C. J. Nalbandian, Z. E. Brown, E. Alvarez, J. L. Gustafson Org. Lett. 2018, 20, 11, 3211-3214; C. Xu, B. Ma, Q. Shen Angew. Chem. Int. Ed. 2014, 53, 9316-9320; P. Zhang, M. Li, X.-S. Xue, C. Xu, Q. Zhao, Y. Liu, H. Wang, Y. Guo, L. Lu, Q. Shen J. Org. Chem. 2016, 81, 7486-7509).

The term «heteroaromatic ring» is used for aromatic rings in which one or more of the carbon atoms in an aromatic ring has been replaced by a heteroatom selected from the group consisting of nitrogen, oxygen, sulfur, selenium and phosphor.

Said at least one aromatic or heteroaromatic ring of compound (A) may be unsubstituted or substituted by one or more organic residues R.

Preferably said organic residue R is selected from the group consisting of fluoro, chloro, bromo, iodo, amino, cyano, hydroxy, nitro, $C_{1-12}$ alkyl, $C_{2-15}$ alkenyl, $C_{2-15}$ alkynyl, $C_{3-15}$ cycloalkyl, $C_{3-15}$ cycloalkenyl, cycloalkynyl, $C_{3-5}$ alkylene, $C_{3-5}$ cycloalkylene, $C_{3-5}$ alkenylene, $C_{3-5}$ alkynylene, halo-$C_{1-6}$ alkyl, hydroxy-$C_{1-6}$ alkyl, halo-$C_{3-15}$ cycloalkyl, $C_{1-10}$ alkoxy, $C_{3-5}$ cycloalkoxy, alkylenedioxy, $C_{1-6}$ acyl, $C_{3-6}$ cycloacyl, $C_{1-6}$ acyloxy, $C_{3-6}$ cycloacyloxy, arylalkyl, heteroarylalkyl, aryl and heteroaryl group and/or may form an annealed ring system with other rings selected from cycloalkyl, aryl and heteroaryl rings.

"Alkyl", whether used alone or as part of another group such as «haloalkyl» or «arylalkyl», means a linear or branched aliphatic hydrocarbon group having a single radical. Examples of alkyl groups include methyl, propyl, isopropyl, butyl, n-butyl, isobutyl, sec-butyl, tert-butyl, pentyl, hexyl, heptyl, cetyl, and the like. The term "lower alkyl" means a linear or branched hydrocarbon group having from one to about twelve carbon atoms, and having a single radical. A branched alkyl means that one or more lower alkyl groups such as methyl, ethyl or propyl are attached to a linear alkyl chain.

The term "haloalkyl" embraces residues wherein any one or more of the alkyl carbon atoms is substituted with a halogen selected from the group consisting of fluoro, chloro, bromo and iodo. Examples of haloalkyl radicals include for example fluoromethyl, difluoromethyl, trifluoromethyl, chloromethyl, dichloromethyl and trichloromethyl.

The term "hydroxyalkyl" embraces residues wherein any one or more of the alkyl carbon atoms is substituted with a hydroxy. Examples of hydroxyalkyl residues include hydroxymethyl, hydroxyethyl, hydroxybutyl, hydroxypropyl.

The term "cycloalkyl" means a non-aromatic mono- or multicyclic ring system of 3 to 15 carbon atoms having a single radical. Preferred monocyclic cycloalkyl rings include cyclopentyl, cyclohexyl and cycloheptyl. Exemplary multicylic cycloalkyl rings include 1-decalin, adamant-(1- or 2-)yl and norbornyl.

As used herein, the term "alkenyl" means an aliphatic hydrocarbon group having a single radical and containing a carbon-carbon double bond and which may be straight or branched having about 2 to about 15 carbon atoms in the chain. A «branched» alkenyl means that one or more lower alkyl groups such as methyl, ethyl or propyl are attached to a linear alkenyl chain. Exemplary alkenyl groups include ethenyl, propenyl, n-butenyl, i-butenyl, 3-methylbut-2-enyl, n-pentenyl, heptenyl, octenyl and decenyl.

The term "cycloalkenyl" means a non-aromatic monocyclic or multicyclic ring system having a single radical and containing a carbon-carbon double bond and having 3 to 15 carbon atoms. Exemplary monocyclic cycloalkenyl rings include cyclopentenyl, cyclohexenyl or cycloheptenyl. An exemplary multicyclic cycloalkenyl ring is norbornenyl.

The term "alkynyl" means an aliphatic hydrocarbon group having a single radical and containing a carbon-carbon triple bond and which may be straight or branched having about 2 to about 15 carbon atoms in the chain. A "branched" alkynyl means that one or more lower alkyl groups such as methyl, ethyl or propyl are attached to a linear alkynyl chain. "Lower alkynyl" means an alkynyl group having about 2 to about 4 carbon atoms in the chain which may be straight or branched.

The term "cycloalkynyl" means a non-aromatic monocyclic or multicyclic ring system having a single radical and containing a carbon-carbon triple bond and having 3 to 10 carbon atoms. An exemplary monocyclic cycloalkynyl ring is cyclooctynyl.

The term "alkylene" means a linear or branched aliphatic hydrocarbon group having two radicals. Exemplary alkylene groups are methylene and ethylene.

The term "alkenylene" means a linear or branched aliphatic hydrocarbon group having at least one carbon-carbon double bond and two radicals.

The term «alkynylene» means a linear or branched aliphatic hydrocarbon group having a single carbon-carbon triple bond and two radicals.

The term «aryl» means an aromatic carbocyclic radical attached to the aromatic or heteroaromatic ring to be nitrated and containing 6 or 10 resonance electrons. Exemplary aryl groups include phenyl and naphthyl.

The term "arylene" means an aromatic carbocyclic radical having two radicals, from which one is attached to the aromatic or heteroaromatic ring to be nitrated, and containing 6 or 10 resonance electrons. Exemplary arylene groups include phenylene and naphthylene.

The term "arylalkyl" means an aryl group as defined above which is substituted with a linear or branched aliphatic hydrocarbon group.

The term "heteroarylalkyl" means a heteroaryl group as defined above to include a 5- to 10-membered aromatic monocyclic or multicyclic ring system containing at least one carbon atom in the ring and containing 6 or 10 resonance electrons in which one or more of the ring atoms is/are element(s) other than carbon, for example nitrogen, oxygen, sulfur, selenium or phosphor, in which the heteroaryl group is substituted with an alkyl group as defined above to include a linear or branched aliphatic hydrocarbon group.

The term "heterocyclic" means cyclic compounds having a single radical from which one is attached to the aromatic or heteroaromatic ring to be nitrated and containing one or more atoms other than carbon in the ring. The ring may be saturated, partially saturated and unsaturated heteroatom-containing radicals, where the heteroatoms may be selected from nitrogen, sulfur and oxygen. Examples of saturated heterocyclic radicals include saturated 3 to 6-membered heteromonocyclic groups containing 1 to 4 nitrogen atoms, such as pyrrolidinyl, imidazolidinyl, piperidino, piperazinyl; saturated 3- to 6-membered heteromonocyclic groups containing 1 to 2 oxygen atoms and 1 to 3 nitrogen atoms, such as thiazolidinyl. Examples of partially saturated heterocyclic radicals include dihydrothiophene, dihydropyran, dihydrofuran.

The term "acyl" means an H—CO— or alkyl-CO— group in which the alkyl group is as previously defined above. Exemplary acyl groups include formyl, acetyl, propanoyl, 2-methylpropanoyl, butanoyl and palmitoyl. "Cycloacyl" means an H—CO— or cycloalkyl-CO— group in which the cycloalkyl group is as previously defined above.

The term "acyloxy" means an acyl-O— group in which the acyl group is as previously defined. The term "cycloacyloxy" means a cycloacyl-O— group in which the cycloacyl group is as previously defined above.

The term "alkoxy" means an alkyl-O— group in which the alkyl group is as previously defined. Exemplary alkoxy groups include methoxy, ethoxy, n-propoxy, i-propoxy, n-butoxy and heptoxy. The term "cycloalkoxy" means a cycloalkyl-O— group in which the cycloalkyl group is as previously defined above. Exemplary cycloalkoxy groups include cyclopentyloxy.

The term "alkylenedioxy" means an R'—O-alkylene-O—R" group in which the alkylene is as defined above, and R' and R" are selected from the group consisting of an alkyl, alkenyl, alkynyl, cycloalkyl, cycloalkenyl, cycloalkynyl, aryl, heteroaryl, heterocyclic, or R' and R" together is a single alkylene, alkenylene, alkynylene, cycloalkylene, cycloalkenylene, cycloalkynylene or arylene group.

The term "amido" or "aminocarbonyl" means —C(O)NH$_2$, as depicted below:

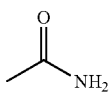

The term "amino" means the group —NH$_2$.

The term "carbamido" or "(aminocarbonyl)amino" is the group having the formula H$_2$NCONH—, as depicted below:

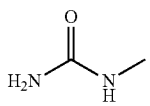

The term "carbamyl" is the group NH$_2$CO—, as depicted below:

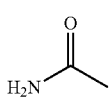

The term "carboxy" or "carboxyl", whether used alone or in combination with other groups, such as "carboxyalkyl", denotes —CO$_2$H, as depicted below:

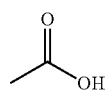

The term "carboxamido" means —NHC(O)—, as depicted below:

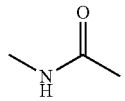

The term "carbonyl", whether used alone or in combination with other terms, such as "alkoxycarbonyl", denotes —(C=O)—. The term "alkoxycarbonyl" means a radical containing an alkoxy radical, as defined above, attached via an oxygen atom to a carbonyl radical.

The term "derivative" means a chemical compound which is changed to such an extent that the structure and properties of the mother compound (A)re not significantly changed.

In one embodiment of the present invention the at least one aromatic or heteroaromatic ring of the compound (A) comprises at least one residue R which is not hydrogen. R is preferably selected from the group as defined above.

Preferably, compound (A) and most preferably the aromatic ring or heteroaromatic ring of the compound (A) comprises at least one acid-sensitive residue. Thus, at least one the acid-sensitive group may be present somewhere in the molecular structure of compound (A) and/or directly on the aromatic or heteroaromatic ring to be nitrated. The term acid-sensitive residue means within the context of the present invention a residue which would be negatively influenced in the presence of an acid, in particular in the presence of H$_2$SO$_4$ and/or HNO$_3$. Most preferably, said acid-sensitive residue is selected from the group consisting of difluoromethoxy, trifluoromethoxy, difluoromethylthio, trifluoromethylthio, chloro, iodo, methoxy, ethoxy, propoxy, butoxy, amino, methylamino, dimethylamino, formyl, methoxycarbonyl, ethoxycarbonyl, tert-butoxycarbonyl, acyl chlorides, acid anhydrides, carboxylate esters, sulfonate esters, alkyl esters, carboxy, ketals, acetals, hydrazones, and 4,4,5,5-tetramethyl-1,3,2-dioxaborolanyl.

Preferably, the aromatic ring or the heteroaromatic ring of compound (A) comprises at least one electron donating group (EDG) as residue. The position of said electron donating group on the aromatic or heteroaromatic ring allows the skilled person to predict the position of the nitration on the ring (Douglas A. Klumpp; Arene Chemistry: Reaction Mechanisms and Methods for Aromatic Compounds, 2016, (John Wiley and Sons, Inc). Said electron donating group is preferably selected from the group consisting of amino, carbamoyl, alkylaminocarbonyl, carboxamido, mercapto, alkylthio, hydroxy, alkoxy, alkyl, acyloxy, aryl, heteroaryl, alkenyl and alkynyl. Most preferably, EDG is selected from the group consisting of amino, methyl, ethyl, phenyl, methoxy and ethoxy. In one preferred embodiment the aromatic or heteroaromatic ring comprises one, two or three EDG which may be the same or different.

Preferably, the aromatic ring or the heteroaromatic ring of compound (A) comprises at least one electron withdrawing group (EWG) as residue. The position of said electron donating group on the aromatic or heteroaromatic ring allows the skilled person to predict the position of the nitration on the ring (Douglas A. Klumpp; Arene Chemistry: Reaction Mechanisms and Methods for Aromatic Compounds, 2016, (John Wiley and Sons, Inc). Said electron withdrawing group is preferably selected from the group consisting of said electron withdrawing group preferably being selected from the group consisting of fluoro, chloro, bromo, iodo, acyl, carboxy, benzoyl, carbonyl, aldehyde, arylsulfonyl, haloalkyl, cyano, and 2,5-dioxopyrrolidinyl. Most preferably, EWD is selected from the group consisting of fluoro, chloro, bromo, iodo, methoxycarbonyl, ethoxycarbonyl, tert-butoxycarbonyl, trifluoromethyl, and difluoromethyl. In one preferred embodiment the aromatic or heteroaromatic ring comprises one, two or three EWD which may be the same or different.

In another preferred embodiment the aromatic or heteroaromatic ring of compound (A) comprises one or two EDG and one or two EWD.

Preferably, compound (A) comprises or consists of a 5- or 6-membered substituted or unsubstituted aromatic or heteroaromatic ring. Thus, in one embodiment of the present invention, said 5- or 6-membered substituted or unsubstituted aromatic or heteroaromatic ring is part of a bigger molecule scaffold. In another embodiment of the present invention, said 5- or 6-membered substituted or unsubstituted aromatic or heteroaromatic ring is compound (A). Preferably, the 5- or 6-membered substituted aromatic or heteroaromatic ring is preferably substituted by one or more acid-sensitive, electron donating and/or electron withdrawing groups.

In another embodiment of the present invention, compound (A) comprises or consists of a fused aromatic or heteroaromatic ring system comprising 2 to 5 aromatic or heteroaromatic rings which may be substituted or not. The substituted fused aromatic or heteroaromatic ring is preferably substituted by one or more acid-sensitive, electron donating and/or electron withdrawing groups.

Preferably, the heteroaromatic ring or ring system is selected from the group consisting of pyrrole, thiophene, furan, imidazole, thiazole, pyrimidine, pyridine, pyrazine, pyridazine, isoxazole, oxazole, indole, isoindole, indolizine, quinoline, isoquinoline, purine, carbazole, dibenzofuran, acridine, purine, guanine, xanthine, uric acid, benzothiophen, benzofuran, dibenzothiophen, thianthren, xanthen, phenoxatiin, isochinoline, phthalazine, 1,8-naphthydrine, quinazoline, quinoxaline, cinnoline, pteridine, perimidine, 1,7-phenanthroline, phenazine, phosphindole, phthalimide, furazan and phosphinoline, most preferably pyridine, pyrimidine, furan and phthalimide. Said heteroaromatic ring or ring system is preferably substituted by one or more acid-sensitive, electron donating and/or electron withdrawing groups.

In another embodiment of the present invention, the aromatic ring or ring system is selected from the group consisting of benzene, pentalene, indene, indan, naphthalene, 1,1'-binaphthalene, azulene, heptalene, biphenylene, as-indacene, s-indacene, acenaphthylene, fluorene phenalene, phenanthrene, anthracene, fluoranthene acephenanthrylene, aceanthrylenetriphenylene, pyrene chrysene, naphthacene, pleiadene, picene and perylene, most preferably benzene. Said aromatic ring or ring system is preferably substituted by one or more acid-sensitive, electron donating and/or electron withdrawing groups.

Preferably, compound (I) in the process of the present invention is compound (Ia)

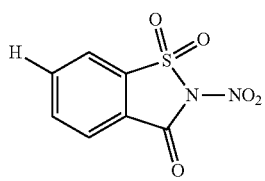

(Ia)

The compound of formula (Ia) can be prepared for example in a quantitative, one-step procedure by reacting concentrated nitric acid and acetic anhydride at ambient temperature with commercially available N-saccharin. The compound of formula (Ia) is a white crystalline powder which is storage stable and can be prepared in a large scale.

Alternatively, compound (I) in the process of the present invention is compound (Ib)

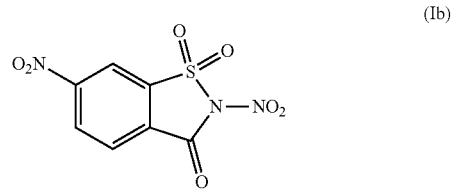 [SMILES: O=C1c2ccc([N+](=O)[O-])cc2S(=O)(=O)N1[N+](=O)[O-]]

(Ib)

Due to the presence of the electron-withdrawing $NO_2$-group, the compound of formula (Ib) is considerably powerful and strongly accelerates the niration reaction, giving the nitrated product within one hour.

Preferably, the reaction is carried out in a solvent selected from the group consisting of hexafluoroisopropanol, acetonitrile, nitromethane, methylenechloride, trifluoroethanol, tetrahydrofuran, hexane, benzene and toluene or mixtures thereof, preferably hexafluoroisopropanol and acetonitrile. Without wishing to be bound by theory, it is assumed that hexafluoroisopropanol catalyzes the nitration reaction.

The process according to the present invention can be carried out in absence of a catalyst. However, it is possible to carry out the reaction in the presence of a catalyst in order to improve the reaction time. Such a catalyst is preferably a proton donating acid or a Lewis acid. The catalytic amount is typically between 5 and 15 mol %, most preferably 10 mol %.

A proton donating acid used in a catalytic amount in the process according to the present invention is preferably selected from the group consisting of acetic acid, trimethylacetic acid, trichloroacetic acid, trifluoroacetic acid, benzoic acid, and mixtures thereof, preferably acetic acid and trimethylacetic acid.

A Lewis acid used in a catalytic amount in the process according to the present invention is preferably an inorganic salt, most preferably selected from the group consisting of iron (II) triflate, iron (III) triflate, magnesium (II) triflate, zinc (II) triflate, cupper (II) triflate, iron (II) bromide, iron (III) bromide and magnesium perchlorate, preferably magnesium perchlorate.

Preferably, the process according to the present invention is carried out under mild conditions. Good results could be obtained at reaction temperature between 50 and 100° C., most preferably between 70 and 90° C. and ideally at 85° C. The reaction time is strongly dependent on compound (A) and the presence of a catalyst. Typically, the reaction time is between 2 h to 24 h.

The process according to the present invention allows a late-stage functionalization of complex molecules and drugs since in particular acid-sensitive groups are not negatively influenced. This allows to synthesize a variety of molecules in a cheaper and more efficient way, and thus can reduce the costs. In addition, it allows to make new analogues and opens up new opportunities for new drugs which could not be synthesized by using traditional approaches. For example, the process according to the present invention allows a late-stage functionalization of complex molecules bearing diverse functionalities, such as for steroids, ibuprofen and other biologically active molecules. Thus, due to the unique stability of the compounds of formula (I) and their compatibility with diverse reaction conditions, the compounds of formula (I) will facilitate drug discovery processes.

The process according to the present invention may be used to prepare a variety of drugs comprising a nitrated aromatic or heteroaromatic ring, such as (3,4-dihydroxy-5-nitrophenyl)(4-methylphenyl)methanone (Tolcapone),
5-nitro-2-furaldehyde semicarbazone (Nitrofural),
D-(−)-2,2-dichloro-N-(β-hydroxy-α-(hydroxymethyl)-p-nitrophenylethyl)acetamide (Chloramphenicol),
3-(5'-nitrofurfuralamino)-2-oxazolidone (Furazolidone),
1-((5-nitro-2-furanyl)methylene)amino-2,4-imidazolidenedione (Nitrofurantoin),
1-[2-(ethylsulfonyl)ethyl]-2-methyl-5-nitro-1H-imidazole (Tinidazole),
1-(2-hydroxy-1-ethyl)-2-methyl-5-nitroimidazole (Metronidazole), [7-nitro-2-[(propan-2-ylamino)methyl]-1,2,3,4-tetrahydroquinolin-6-yl]methanol (Oxamniquine),
5-nitro-8-hydroxyquinoline (Nitroxoline), trinitrophenol (picric acid),
4-nitrophenyl phosphate, p-nitrophenol, 2,4-dinitrophenol,
(6S)-2-nitro-6-[[4-(trifluoromethoxy)phenyl]methoxy]-6,7-dihydro-5H-imidazo[2,1-b][1,3]oxazine (Pretomanid),
(2-bromoethyl)({[(2-bromoethyl)amino][(1-methyl-2-nitro-1H-imidazol-5-yl)methoxy]phosphoryl})amine (Evofosfamide),
2,2-dibromo-N-[(1R,2R)-1,3-dihydroxy-1-(4-nitrophenyl)propan-2-yl]acetamide (Bromamphenicol),
4-[(2R,3R)-2-(2,2-dichloroacetamido)-3-hydroxy-3-(4-nitrophenyl)propoxy]-4-oxobutanoic acid (Chloramphenicol succinate),
2,2-dichloro-N-[(1R,2R)-1,3-dihydroxy-1-(4-methanesulfonylphenyl)propan-2-yl]acetamide (Thiamphenicol),
2-[benzyl(phenyl)amino]ethyl 5-(5,5-dimethyl-2-oxo-1,3,2λ⁵-dioxaphosphinan-2-yl)-2,6-dimethyl-4-(3-nitrophenyl)-,1,4-dihydropyridine-3-carboxylate (Efonidipine),
1-(4-{[(2R)-2-methyl-6-nitro-2H, 3H-imidazo[2,1-b][1,3]oxazol-2-yl]methoxy}phenyl)-4-[4-(trifluoromethoxy)phenoxy]piperidine (Delamanid),
1-methoxy-3-(2-nitro-1H-imidazol-1-yl)propan-2-ol (Misonidazole),
3-methyl-4-[(E)-[(5-nitrofuran-2-yl)methylidene]amino]-1lambda6-thiomorpholine-1,1-dione (Nifurtimox),
1-chloro-2,4-dinitrobenzene (Dinitrochlorobenzene),
N-benzyl-2-(2-nitro-1H-imidazol-1-yl)ethanimidic acid (Benznidazole),
4-(2-(5-nitro-1H-imidazol-1-yl)ethyl)morpholine (Nimorazole),
1-methyl-2-{[4-(methylsulfanyl)phenoxy]methyl}-5-nitro-1H-imidazole (Fexinidazole),
1-(2-nitro-1H-imidazol-1-yl)-3-(piperidin-1-yl)propan-2-ol (Pimonidazole),
N-(2-hydroxyethyl)-2-(2-nitro-1H-imidazol-1-yl)ethanimidic acid (Etanidazole),
1-(2-methyl-5-nitro-1H-imidazol-1-yl)propan-2-ol (Secnidazole), 1-chloro-3-(2-methyl-5-nitro-1H-imidazol-1-yl)propan-2-ol (Ornidazole),
N-[2-(cyclohexyloxy)-4-nitrophenyl]methanesulfonamide (NS-398) and
(2R,3R)-2-(2,2-dichloroacetamido)-3-hydroxy-3-(4-nitrophenyl)propyl hexadecanoate (Chloramphenicol palmitate).
2-Nitro-1-(4-nitrophenoxy)-4-(trifluoromethyl)benzene (Fluorodifen)
6-Nitro coumarin
7-Methyl-8-nitroquinoline
2-Nitro-1H-imidazole (Azomycin)
1-[2-(Ethylsulfonyl)ethyl]-2-methyl-5-nitro-1H-imidazole (Tinidazole)
5-(1-Methyl-5-nitro-1H-imidazol-2-yl)-1,3,4-thiadiazol-2-amine (Megazole)
4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide (Ventoclax)
5-Chlor-N-(2-chlor-4-nitrophenyl)-2-hydroxybenzamide (Niclosamide)
(E)-2-Cyano-3-(3,4-dihydroxy-5-nitro-phenyl)-N,N-diethyl-prop-2-enamide (Entacapone)
2-(4-nitrophenyl)propan-2-yl (6-(benzyloxy)-9H-purin-2-yl)carbamate (O6-Benzylguanine derivative)
Methyl 2-(6-nitro-4-oxoquinolin-1(4H)-yl)acetate (FSL-61)

In a preferred embodiment, the process according to the present invention is used to prepare the compound of formula (X) in high amounts:

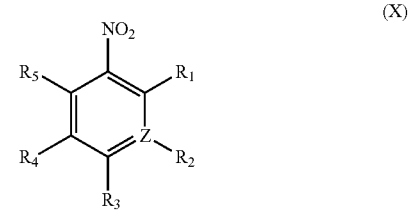

| Compound X, wherein Z is C | | | | | Compound X, wherein Z is N | | | |
|---|---|---|---|---|---|---|---|---|
| $R_1$ | $R_2$ | $R_3$ | $R_4$ | $R_5$ | $R_1$ | $R_3$ | $R_4$ | $R_5$ |
| H | H | H | H | H | H | H | H | H |
| H | H | F | H | H | H | F | H | H |
| H | H | Cl | H | H | H | Cl | H | H |
| H | H | Br | H | H | H | Br | H | H |
| H | H | I | H | H | H | I | H | H |
| H | H | methyl | H | H | H | methyl | H | H |
| H | H | ethyl | H | H | H | ethyl | H | H |
| H | H | propyl | H | H | H | propyl | H | H |
| H | H | iso-propyl | H | H | H | iso-propyl | H | H |
| H | H | butyl | H | H | H | butyl | H | H |
| H | H | sec-butyl | H | H | H | sec-butyl | H | H |
| H | H | tert-butyl | H | H | H | tert-butyl | H | H |
| H | H | $OCF_3$ | H | H | H | $OCF_3$ | H | H |

-continued

| Compound X, wherein Z is C | | | | | Compound X, wherein Z is N | | | |
|---|---|---|---|---|---|---|---|---|
| $R_1$ | $R_2$ | $R_3$ | $R_4$ | $R_5$ | $R_1$ | $R_3$ | $R_4$ | $R_5$ |
| H | H | $SCF_3$ | H | H | H | $SCF_3$ | H | H |
| H | H | $N(CH_3)_2$ | H | H | H | $N(CH_3)_2$ | H | H |
| H | H | phenyl | H | H | H | phenyl | H | H |
| H | H | methoxy | H | H | H | methoxy | H | H |
| H | H | ethoxy | H | H | H | ethoxy | H | H |
| H | H | propoxy | H | H | H | propoxy | H | H |
| H | $C(O)CH_3$ | F | H | H | F | F | H | H |
| H | $C(O)CH_3$ | Cl | H | H | F | Cl | H | H |
| H | $C(O)CH_3$ | Br | H | H | F | Br | H | H |
| H | $C(O)CH_3$ | I | H | H | F | I | H | H |
| H | $C(O)CH_3$ | methyl | H | H | F | methyl | H | H |
| H | $C(O)CH_3$ | ethyl | H | H | F | ethyl | H | H |
| H | $C(O)CH_3$ | propyl | H | H | F | propyl | H | H |
| H | $C(O)CH_3$ | iso-propyl | H | H | F | iso-propyl | H | H |
| H | $C(O)CH_3$ | butyl | H | H | F | butyl | H | H |
| H | $C(O)CH_3$ | sec-butyl | H | H | F | sec-butyl | H | H |
| H | $C(O)CH_3$ | tert-butyl | H | H | F | tert-butyl | H | H |
| H | $C(O)CH_3$ | $OCF_3$ | H | H | F | $OCF_3$ | H | H |
| H | $C(O)CH_3$ | $SCF_3$ | H | H | F | $SCF_3$ | H | H |
| H | $C(O)CH_3$ | $N(CH_3)_2$ | H | H | F | $N(CH_3)_2$ | H | H |
| H | $C(O)CH_3$ | phenyl | H | H | F | phenyl | H | H |
| H | $C(O)CH_3$ | methoxy | H | H | F | methoxy | H | H |
| H | $C(O)CH_3$ | ethoxy | H | H | F | ethoxy | H | H |
| H | $C(O)CH_3$ | propoxy | H | H | F | propoxy | H | H |
| H | $CF_3$ | H | H | H | Cl | F | H | H |
| H | $CF_3$ | F | H | H | Cl | Cl | H | H |
| H | $CF_3$ | Cl | H | H | Cl | Br | H | H |
| H | $CF_3$ | Br | H | H | Cl | I | H | H |
| H | $CF_3$ | I | H | H | Cl | methyl | H | H |
| H | $CF_3$ | methyl | H | H | Cl | ethyl | H | H |
| H | $CF_3$ | ethyl | H | H | Cl | propyl | H | H |
| H | $CF_3$ | propyl | H | H | Cl | iso-propyl | H | H |
| H | $CF_3$ | iso-propyl | H | H | Cl | butyl | H | H |
| H | $CF_3$ | butyl | H | H | Cl | sec-butyl | H | H |
| H | $CF_3$ | sec-butyl | H | H | Cl | tert-butyl | H | H |
| H | $CF_3$ | tert-butyl | H | H | Cl | $OCF_3$ | H | H |
| H | $CF_3$ | $OCF_3$ | H | H | Cl | $SCF_3$ | H | H |
| H | $CF_3$ | $SCF_3$ | H | H | Cl | $N(CH_3)_2$ | H | H |
| H | $CF_3$ | $N(CH_3)_2$ | H | H | Cl | phenyl | H | H |
| H | $CF_3$ | phenyl | H | H | Cl | methoxy | H | H |
| H | $CF_3$ | methoxy | H | H | Cl | ethoxy | H | H |
| H | $CF_3$ | ethoxy | H | H | Cl | propoxy | H | H |
| H | $CF_3$ | propoxy | H | H | I | F | H | H |
| F | CHO | F | H | H | I | Cl | H | H |
| H | CHO | Cl | H | H | I | Br | H | H |
| H | CHO | Br | H | H | I | I | H | H |
| H | CHO | I | H | H | I | methyl | H | H |
| H | CHO | methyl | H | H | I | ethyl | H | H |
| H | CHO | ethyl | H | H | I | propyl | H | H |
| H | CHO | propyl | H | H | I | iso-propyl | H | H |
| H | CHO | iso-propyl | H | H | I | butyl | H | H |
| H | CHO | butyl | H | H | I | sec-butyl | H | H |
| H | CHO | sec-butyl | H | H | I | tert-butyl | H | H |
| H | CHO | tert-butyl | H | H | I | $OCF_3$ | H | H |
| H | CHO | $OCF_3$ | H | H | I | $SCF_3$ | H | H |
| H | CHO | $SCF_3$ | H | H | I | $N(CH_3)_2$ | H | H |
| H | CHO | $N(CH_3)_2$ | H | H | I | phenyl | H | H |
| H | CHO | phenyl | H | H | I | methoxy | H | H |
| H | CHO | methoxy | H | H | I | ethoxy | H | H |
| H | CHO | ethoxy | H | H | I | propoxy | H | H |
| H | CHO | propoxy | H | H | methyl | F | H | H |
| F | CHO | F | H | H | methyl | Cl | H | H |
| H | $NO_2$ | Cl | H | H | methyl | Br | H | H |
| H | $NO_2$ | Br | H | H | methyl | I | H | H |
| H | $NO_2$ | I | H | H | methyl | methyl | H | H |
| H | $NO_2$ | methyl | H | H | methyl | ethyl | H | H |
| H | $NO_2$ | ethyl | H | H | methyl | propyl | H | H |
| H | $NO_2$ | propyl | H | H | methyl | iso-propyl | H | H |
| H | $NO_2$ | iso-propyl | H | H | methyl | butyl | H | H |
| H | $NO_2$ | butyl | H | H | methyl | sec-butyl | H | H |
| H | $NO_2$ | sec-butyl | H | H | methyl | tert-butyl | H | H |
| H | $NO_2$ | tert-butyl | H | H | methyl | $OCF_3$ | H | H |
| H | $NO_2$ | $OCF_3$ | H | H | methyl | $SCF_3$ | H | H |
| H | $NO_2$ | $SCF_3$ | H | H | methyl | $N(CH_3)_2$ | H | H |
| H | $NO_2$ | $N(CH_3)_2$ | H | H | methyl | phenyl | H | H |

-continued

| Compound X, wherein Z is C | | | | | Compound X, wherein Z is N | | | |
| --- | --- | --- | --- | --- | --- | --- | --- | --- |
| R₁ | R₂ | R₃ | R₄ | R₅ | R₁ | R₃ | R₄ | R₅ |
| H | NO₂ | phenyl | H | H | methyl | methoxy | H | H |
| H | NO₂ | methoxy | H | H | methyl | ethoxy | H | H |
| H | NO₂ | ethoxy | H | H | methyl | propoxy | H | H |
| H | NO₂ | propoxy | H | H | ethyl | F | H | H |
| H | TMDOB | H | H | H | ethyl | Cl | H | H |
| H | TMDOB | F | H | H | ethyl | Br | H | H |
| H | TMDOB | Cl | H | H | ethyl | I | H | H |
| H | TMDOB | Br | H | H | ethyl | methyl | H | H |
| H | TMDOB | I | H | H | ethyl | ethyl | H | H |
| H | TMDOB | methyl | H | H | ethyl | propyl | H | H |
| H | TMDOB | ethyl | H | H | ethyl | iso-propyl | H | H |
| H | TMDOB | propyl | H | H | ethyl | butyl | H | H |
| H | TMDOB | iso-propyl | H | H | ethyl | sec-butyl | H | H |
| H | TMDOB | butyl | H | H | ethyl | tert-butyl | H | H |
| H | TMDOB | sec-butyl | H | H | ethyl | OCF₃ | H | H |
| H | TMDOB | tert-butyl | H | H | ethyl | SCF₃ | H | H |
| H | TMDOB | OCF₃ | H | H | ethyl | N(CH₃)₂ | H | H |
| H | TMDOB | SCF₃ | H | H | ethyl | phenyl | H | H |
| H | TMDOB | N(CH₃)₂ | H | H | ethyl | methoxy | H | H |
| H | TMDOB | phenyl | H | H | ethyl | ethoxy | H | H |
| H | TMDOB | methoxy | H | H | ethyl | propoxy | H | H |
| H | TMDOB | ethoxy | H | H | propyl | F | H | H |
| H | TMDOB | propoxy | H | H | propyl | Cl | H | H |
| F | H | F | H | H | propyl | Br | H | H |
| F | H | Cl | H | H | propyl | I | H | H |
| F | H | Br | H | H | propyl | methyl | H | H |
| F | H | I | H | H | propyl | ethyl | H | H |
| F | H | methyl | H | H | propyl | propyl | H | H |
| F | H | ethyl | H | H | propyl | iso-propyl | H | H |
| F | H | propyl | H | H | propyl | butyl | H | H |
| F | H | iso-propyl | H | H | propyl | sec-butyl | H | H |
| F | H | butyl | H | H | propyl | tert-butyl | H | H |
| F | H | sec-butyl | H | H | propyl | OCF₃ | H | H |
| F | H | tert-butyl | H | H | propyl | SCF₃ | H | H |
| F | H | OCF₃ | H | H | propyl | N(CH₃)₂ | H | H |
| F | H | SCF₃ | H | H | propyl | phenyl | H | H |
| F | H | N(CH₃)₂ | H | H | propyl | methoxy | H | H |
| F | H | phenyl | H | H | propyl | ethoxy | H | H |
| F | H | methoxy | H | H | propyl | propoxy | H | H |
| F | H | ethoxy | H | H | iso-propyl | F | H | H |
| F | H | propoxy | H | H | iso-propyl | Cl | H | H |
| Cl | H | F | H | H | iso-propyl | Br | H | H |
| Cl | H | Cl | H | H | iso-propyl | I | H | H |
| Cl | H | Br | H | H | iso-propyl | methyl | H | H |
| Cl | H | I | H | H | iso-propyl | ethyl | H | H |
| Cl | H | methyl | H | H | iso-propyl | propyl | H | H |
| Cl | H | ethyl | H | H | iso-propyl | iso-propyl | H | H |
| Cl | H | propyl | H | H | iso-propyl | butyl | H | H |
| Cl | H | iso-propyl | H | H | iso-propyl | sec-butyl | H | H |
| Cl | H | butyl | H | H | iso-propyl | tert-butyl | H | H |
| Cl | H | sec-butyl | H | H | iso-propyl | OCF₃ | H | H |
| Cl | H | tert-butyl | H | H | iso-propyl | SCF₃ | H | H |
| Cl | H | OCF₃ | H | H | iso-propyl | N(CH₃)₂ | H | H |
| Cl | H | SCF₃ | H | H | iso-propyl | phenyl | H | H |
| Cl | H | N(CH₃)₂ | H | H | iso-propyl | methoxy | H | H |
| Cl | H | phenyl | H | H | iso-propyl | ethoxy | H | H |
| Cl | H | methoxy | H | H | iso-propyl | propoxy | H | H |
| Cl | H | ethoxy | H | H | butyl | F | H | H |
| Cl | H | propoxy | H | H | butyl | Cl | H | H |
| I | H | F | H | H | butyl | Br | H | H |
| I | H | Cl | H | H | butyl | I | H | H |
| I | H | Br | H | H | butyl | methyl | H | H |
| I | H | I | H | H | butyl | ethyl | H | H |
| I | H | methyl | H | H | butyl | propyl | H | H |
| I | H | ethyl | H | H | butyl | iso-propyl | H | H |
| I | H | propyl | H | H | butyl | butyl | H | H |
| I | H | iso-propyl | H | H | butyl | sec-butyl | H | H |
| I | H | butyl | H | H | butyl | tert-butyl | H | H |
| I | H | sec-butyl | H | H | butyl | OCF₃ | H | H |
| I | H | tert-butyl | H | H | butyl | SCF₃ | H | H |
| I | H | OCF₃ | H | H | butyl | N(CH₃)₂ | H | H |
| I | H | SCF₃ | H | H | butyl | phenyl | H | H |
| I | H | N(CH₃)₂ | H | H | butyl | methoxy | H | H |
| I | H | phenyl | H | H | butyl | ethoxy | H | H |
| I | H | methoxy | H | H | butyl | propoxy | H | H |

-continued

| Compound X, wherein Z is C | | | | | Compound X, wherein Z is N | | | |
|---|---|---|---|---|---|---|---|---|
| R$_1$ | R$_2$ | R$_3$ | R$_4$ | R$_5$ | R$_1$ | R$_3$ | R$_4$ | R$_5$ |
| I | H | ethoxy | H | H | sec-butyl | F | H | H |
| I | H | propoxy | H | H | sec-butyl | Cl | H | H |
| methyl | H | F | H | H | sec-butyl | Br | H | H |
| methyl | H | Cl | H | H | sec-butyl | I | H | H |
| methyl | H | Br | H | H | sec-butyl | methyl | H | H |
| methyl | H | I | H | H | sec-butyl | ethyl | H | H |
| methyl | H | methyl | H | H | sec-butyl | propyl | H | H |
| methyl | H | ethyl | H | H | sec-butyl | iso-propyl | H | H |
| methyl | H | propyl | H | H | sec-butyl | butyl | H | H |
| methyl | H | iso-propyl | H | H | sec-butyl | sec-butyl | H | H |
| methyl | H | butyl | H | H | sec-butyl | tert-butyl | H | H |
| methyl | H | sec-butyl | H | H | sec-butyl | OCF$_3$ | H | H |
| methyl | H | tert-butyl | H | H | sec-butyl | SCF$_3$ | H | H |
| methyl | H | OCF$_3$ | H | H | sec-butyl | N(CH$_3$)$_2$ | H | H |
| methyl | H | SCF$_3$ | H | H | sec-butyl | phenyl | H | H |
| methyl | H | N(CH$_3$)$_2$ | H | H | sec-butyl | methoxy | H | H |
| methyl | H | phenyl | H | H | sec-butyl | ethoxy | H | H |
| methyl | H | methoxy | H | H | sec-butyl | propoxy | H | H |
| methyl | H | ethoxy | H | H | tert-butyl | F | H | H |
| methyl | H | propoxy | H | H | tert-butyl | Cl | H | H |
| ethyl | H | F | H | H | tert-butyl | Br | H | H |
| ethyl | H | Cl | H | H | tert-butyl | I | H | H |
| ethyl | H | Br | H | H | tert-butyl | methyl | H | H |
| ethyl | H | I | H | H | tert-butyl | ethyl | H | H |
| ethyl | H | methyl | H | H | tert-butyl | propyl | H | H |
| ethyl | H | ethyl | H | H | tert-butyl | iso-propyl | H | H |
| ethyl | H | propyl | H | H | tert-butyl | butyl | H | H |
| ethyl | H | iso-propyl | H | H | tert-butyl | sec-butyl | H | H |
| ethyl | H | butyl | H | H | tert-butyl | tert-butyl | H | H |
| ethyl | H | sec-butyl | H | H | tert-butyl | OCF$_3$ | H | H |
| ethyl | H | tert-butyl | H | H | tert-butyl | SCF$_3$ | H | H |
| ethyl | H | OCF$_3$ | H | H | tert-butyl | N(CH$_3$)$_2$ | H | H |
| ethyl | H | SCF$_3$ | H | H | tert-butyl | phenyl | H | H |
| ethyl | H | N(CH$_3$)$_2$ | H | H | tert-butyl | methoxy | H | H |
| ethyl | H | phenyl | H | H | tert-butyl | ethoxy | H | H |
| ethyl | H | methoxy | H | H | tert-butyl | propoxy | H | H |
| ethyl | H | ethoxy | H | H | OCF$_3$ | F | H | H |
| ethyl | H | propoxy | H | H | OCF$_3$ | Cl | H | H |
| propyl | H | F | H | H | OCF$_3$ | Br | H | H |
| propyl | H | Cl | H | H | OCF$_3$ | I | H | H |
| propyl | H | Br | H | H | OCF$_3$ | methyl | H | H |
| propyl | H | I | H | H | OCF$_3$ | ethyl | H | H |
| propyl | H | methyl | H | H | OCF$_3$ | propyl | H | H |
| propyl | H | ethyl | H | H | OCF$_3$ | iso-propyl | H | H |
| propyl | H | propyl | H | H | OCF$_3$ | butyl | H | H |
| propyl | H | iso-propyl | H | H | OCF$_3$ | sec-butyl | H | H |
| propyl | H | butyl | H | H | OCF$_3$ | tert-butyl | H | H |
| propyl | H | sec-butyl | H | H | OCF$_3$ | OCF$_3$ | H | H |
| propyl | H | tert-butyl | H | H | OCF$_3$ | SCF$_3$ | H | H |
| propyl | H | OCF$_3$ | H | H | OCF$_3$ | N(CH$_3$)$_2$ | H | H |
| propyl | H | SCF$_3$ | H | H | OCF$_3$ | phenyl | H | H |
| propyl | H | N(CH$_3$)$_2$ | H | H | OCF$_3$ | methoxy | H | H |
| propyl | H | phenyl | H | H | OCF$_3$ | ethoxy | H | H |
| propyl | H | methoxy | H | H | OCF$_3$ | propoxy | H | H |
| propyl | H | ethoxy | H | H | SCF$_3$ | F | H | H |
| propyl | H | propoxy | H | H | SCF$_3$ | Cl | H | H |
| iso-propyl | H | F | H | H | SCF$_3$ | Br | H | H |
| iso-propyl | H | Cl | H | H | SCF$_3$ | I | H | H |
| iso-propyl | H | Br | H | H | SCF$_3$ | methyl | H | H |
| iso-propyl | H | I | H | H | SCF$_3$ | ethyl | H | H |
| iso-propyl | H | methyl | H | H | SCF$_3$ | propyl | H | H |
| iso-propyl | H | ethyl | H | H | SCF$_3$ | iso-propyl | H | H |
| iso-propyl | H | propyl | H | H | SCF$_3$ | butyl | H | H |
| iso-propyl | H | iso-propyl | H | H | SCF$_3$ | sec-butyl | H | H |
| iso-propyl | H | butyl | H | H | SCF$_3$ | tert-butyl | H | H |
| iso-propyl | H | sec-butyl | H | H | SCF$_3$ | OCF$_3$ | H | H |
| iso-propyl | H | tert-butyl | H | H | SCF$_3$ | SCF$_3$ | H | H |
| iso-propyl | H | OCF$_3$ | H | H | SCF$_3$ | N(CH$_3$)$_2$ | H | H |
| iso-propyl | H | SCF$_3$ | H | H | SCF$_3$ | phenyl | H | H |
| iso-propyl | H | N(CH$_3$)$_2$ | H | H | SCF$_3$ | methoxy | H | H |
| iso-propyl | H | phenyl | H | H | SCF$_3$ | ethoxy | H | H |
| iso-propyl | H | methoxy | H | H | SCF$_3$ | propoxy | H | H |
| iso-propyl | H | ethoxy | H | H | N(CH$_3$)$_2$ | F | H | H |
| iso-propyl | H | propoxy | H | H | N(CH$_3$)$_2$ | Cl | H | H |
| butyl | H | F | H | H | N(CH$_3$)$_2$ | Br | H | H |

|  | Compound X, wherein Z is C | | | | Compound X, wherein Z is N | | | |
| --- | --- | --- | --- | --- | --- | --- | --- | --- |
| R₁ | R₂ | R₃ | R₄ | R₅ | R₁ | R₃ | R₄ | R₅ |
| butyl | H | Cl | H | H | N(CH₃)₂ | I | H | H |
| butyl | H | Br | H | H | N(CH₃)₂ | methyl | H | H |
| butyl | H | I | H | H | N(CH₃)₂ | ethyl | H | H |
| butyl | H | methyl | H | H | N(CH₃)₂ | propyl | H | H |
| butyl | H | ethyl | H | H | N(CH₃)₂ | iso-propyl | H | H |
| butyl | H | propyl | H | H | N(CH₃)₂ | butyl | H | H |
| butyl | H | iso-propyl | H | H | N(CH₃)₂ | sec-butyl | H | H |
| butyl | H | butyl | H | H | N(CH₃)₂ | tert-butyl | H | H |
| butyl | H | sec-butyl | H | H | N(CH₃)₂ | OCF₃ | H | H |
| butyl | H | tert-butyl | H | H | N(CH₃)₂ | SCF₃ | H | H |
| butyl | H | OCF₃ | H | H | N(CH₃)₂ | N(CH₃)₂ | H | H |
| butyl | H | SCF₃ | H | H | N(CH₃)₂ | phenyl | H | H |
| butyl | H | N(CH₃)₂ | H | H | N(CH₃)₂ | methoxy | H | H |
| butyl | H | phenyl | H | H | N(CH₃)₂ | ethoxy | H | H |
| butyl | H | methoxy | H | H | N(CH₃)₂ | propoxy | H | H |
| butyl | H | ethoxy | H | H | phenyl | F | H | H |
| butyl | H | propoxy | H | H | phenyl | Cl | H | H |
| sec-butyl | H | F | H | H | phenyl | Br | H | H |
| sec-butyl | H | Cl | H | H | phenyl | I | H | H |
| sec-butyl | H | Br | H | H | phenyl | methyl | H | H |
| sec-butyl | H | I | H | H | phenyl | ethyl | H | H |
| sec-butyl | H | methyl | H | H | phenyl | propyl | H | H |
| sec-butyl | H | ethyl | H | H | phenyl | iso-propyl | H | H |
| sec-butyl | H | propyl | H | H | phenyl | butyl | H | H |
| sec-butyl | H | iso-propyl | H | H | phenyl | sec-butyl | H | H |
| sec-butyl | H | butyl | H | H | phenyl | tert-butyl | H | H |
| sec-butyl | H | sec-butyl | H | H | phenyl | OCF₃ | H | H |
| sec-butyl | H | tert-butyl | H | H | phenyl | SCF₃ | H | H |
| sec-butyl | H | OCF₃ | H | H | phenyl | N(CH₃)₂ | H | H |
| sec-butyl | H | SCF₃ | H | H | phenyl | phenyl | H | H |
| sec-butyl | H | N(CH₃)₂ | H | H | phenyl | methoxy | H | H |
| sec-butyl | H | phenyl | H | H | phenyl | ethoxy | H | H |
| sec-butyl | H | methoxy | H | H | phenyl | propoxy | H | H |
| sec-butyl | H | ethoxy | H | H | methoxy | F | H | H |
| sec-butyl | H | propoxy | H | H | methoxy | Cl | H | H |
| tert-butyl | H | F | H | H | methoxy | Br | H | H |
| tert-butyl | H | Cl | H | H | methoxy | I | H | H |
| tert-butyl | H | Br | H | H | methoxy | methyl | H | H |
| tert-butyl | H | I | H | H | methoxy | ethyl | H | H |
| tert-butyl | H | methyl | H | H | methoxy | propyl | H | H |
| tert-butyl | H | ethyl | H | H | methoxy | iso-propyl | H | H |
| tert-butyl | H | propyl | H | H | methoxy | butyl | H | H |
| tert-butyl | H | iso-propyl | H | H | methoxy | sec-butyl | H | H |
| tert-butyl | H | butyl | H | H | methoxy | tert-butyl | H | H |
| tert-butyl | H | sec-butyl | H | H | methoxy | OCF₃ | H | H |
| tert-butyl | H | tert-butyl | H | H | methoxy | SCF₃ | H | H |
| tert-butyl | H | OCF₃ | H | H | methoxy | N(CH₃)₂ | H | H |
| tert-butyl | H | SCF₃ | H | H | methoxy | phenyl | H | H |
| tert-butyl | H | N(CH₃)₂ | H | H | methoxy | methoxy | H | H |
| tert-butyl | H | phenyl | H | H | methoxy | ethoxy | H | H |
| tert-butyl | H | methoxy | H | H | methoxy | propoxy | H | H |
| tert-butyl | H | ethoxy | H | H | ethoxy | F | H | H |
| tert-butyl | H | propoxy | H | H | ethoxy | Cl | H | H |
| OCF₃ | H | F | H | H | ethoxy | Br | H | H |
| OCF₃ | H | Cl | H | H | ethoxy | I | H | H |
| OCF₃ | H | Br | H | H | ethoxy | methyl | H | H |
| OCF₃ | H | I | H | H | ethoxy | ethyl | H | H |
| OCF₃ | H | methyl | H | H | ethoxy | propyl | H | H |
| OCF₃ | H | ethyl | H | H | ethoxy | iso-propyl | H | H |
| OCF₃ | H | propyl | H | H | ethoxy | butyl | H | H |
| OCF₃ | H | iso-propyl | H | H | ethoxy | sec-butyl | H | H |
| OCF₃ | H | butyl | H | H | ethoxy | tert-butyl | H | H |
| OCF₃ | H | sec-butyl | H | H | ethoxy | OCF₃ | H | H |
| OCF₃ | H | tert-butyl | H | H | ethoxy | SCF₃ | H | H |
| OCF₃ | H | OCF₃ | H | H | ethoxy | N(CH₃)₂ | H | H |
| OCF₃ | H | SCF₃ | H | H | ethoxy | phenyl | H | H |
| OCF₃ | H | N(CH₃)₂ | H | H | ethoxy | methoxy | H | H |
| OCF₃ | H | phenyl | H | H | ethoxy | ethoxy | H | H |
| OCF₃ | H | methoxy | H | H | ethoxy | propoxy | H | H |
| OCF₃ | H | ethoxy | H | H | propoxy | F | H | H |
| OCF₃ | H | propoxy | H | H | propoxy | Cl | H | H |
| SCF₃ | H | F | H | H | propoxy | Br | H | H |
| SCF₃ | H | Cl | H | H | propoxy | I | H | H |
| SCF₃ | H | Br | H | H | propoxy | methyl | H | H |
| SCF₃ | H | I | H | H | propoxy | ethyl | H | H |

-continued

| Compound X, wherein Z is C | | | | | Compound X, wherein Z is N | | | |
|---|---|---|---|---|---|---|---|---|
| $R_1$ | $R_2$ | $R_3$ | $R_4$ | $R_5$ | $R_1$ | $R_3$ | $R_4$ | $R_5$ |
| $SCF_3$ | H | methyl | H | H | propoxy | propyl | H | H |
| $SCF_3$ | H | ethyl | H | H | propoxy | iso-propyl | H | H |
| $SCF_3$ | H | propyl | H | H | propoxy | butyl | H | H |
| $SCF_3$ | H | iso-propyl | H | H | propoxy | sec-butyl | H | H |
| $SCF_3$ | H | butyl | H | H | propoxy | tert-butyl | H | H |
| $SCF_3$ | H | sec-butyl | H | H | propoxy | $OCF_3$ | H | H |
| $SCF_3$ | H | tert-butyl | H | H | propoxy | $SCF_3$ | H | H |
| $SCF_3$ | H | $OCF_3$ | H | H | propoxy | $N(CH_3)_2$ | H | H |
| $SCF_3$ | H | $SCF_3$ | H | H | propoxy | phenyl | H | H |
| $SCF_3$ | H | $N(CH_3)_2$ | H | H | propoxy | methoxy | H | H |
| $SCF_3$ | H | phenyl | H | H | propoxy | ethoxy | H | H |
| $SCF_3$ | H | methoxy | H | H | propoxy | propoxy | H | H |
| $SCF_3$ | H | ethoxy | H | H | H | H | $NO_2$ | H |
| $SCF_3$ | H | propoxy | H | H | H | F | $NO_2$ | H |
| $N(CH_3)_2$ | H | F | H | H | H | Cl | $NO_2$ | H |
| $N(CH_3)_2$ | H | Cl | H | H | H | Br | $NO_2$ | H |
| $N(CH_3)_2$ | H | Br | H | H | H | I | $NO_2$ | H |
| $N(CH_3)_2$ | H | I | H | H | H | methyl | $NO_2$ | H |
| $N(CH_3)_2$ | H | methyl | H | H | H | ethyl | $NO_2$ | H |
| $N(CH_3)_2$ | H | ethyl | H | H | H | propyl | $NO_2$ | H |
| $N(CH_3)_2$ | H | propyl | H | H | H | iso-propyl | $NO_2$ | H |
| $N(CH_3)_2$ | H | iso-propyl | H | H | H | butyl | $NO_2$ | H |
| $N(CH_3)_2$ | H | butyl | H | H | H | sec-butyl | $NO_2$ | H |
| $N(CH_3)_2$ | H | sec-butyl | H | H | H | tert-butyl | $NO_2$ | H |
| $N(CH_3)_2$ | H | tert-butyl | H | H | H | $OCF_3$ | $NO_2$ | H |
| $N(CH_3)_2$ | H | $OCF_3$ | H | H | H | $SCF_3$ | $NO_2$ | H |
| $N(CH_3)_2$ | H | $SCF_3$ | H | H | H | $N(CH_3)_2$ | $NO_2$ | H |
| $N(CH_3)_2$ | H | $N(CH_3)_2$ | H | H | H | phenyl | $NO_2$ | H |
| $N(CH_3)_2$ | H | phenyl | H | H | H | methoxy | $NO_2$ | H |
| $N(CH_3)_2$ | H | methoxy | H | H | H | ethoxy | $NO_2$ | H |
| $N(CH_3)_2$ | H | ethoxy | H | H | H | propoxy | $NO_2$ | H |
| $N(CH_3)_2$ | H | propoxy | H | H | F | F | $NO_2$ | H |
| phenyl | H | F | H | H | F | Cl | $NO_2$ | H |
| phenyl | H | Cl | H | H | F | Br | $NO_2$ | H |
| phenyl | H | Br | H | H | F | I | $NO_2$ | H |
| phenyl | H | I | H | H | F | methyl | $NO_2$ | H |
| phenyl | H | methyl | H | H | F | ethyl | $NO_2$ | H |
| phenyl | H | ethyl | H | H | F | propyl | $NO_2$ | H |
| phenyl | H | propyl | H | H | F | iso-propyl | $NO_2$ | H |
| phenyl | H | iso-propyl | H | H | F | butyl | $NO_2$ | H |
| phenyl | H | butyl | H | H | F | sec-butyl | $NO_2$ | H |
| phenyl | H | sec-butyl | H | H | F | tert-butyl | $NO_2$ | H |
| phenyl | H | tert-butyl | H | H | F | $OCF_3$ | $NO_2$ | H |
| phenyl | H | $OCF_3$ | H | H | F | $SCF_3$ | $NO_2$ | H |
| phenyl | H | $SCF_3$ | H | H | F | $N(CH_3)_3$ | $NO_2$ | H |
| phenyl | H | $N(CH_3)_2$ | H | H | F | phenyl | $NO_2$ | H |
| phenyl | H | phenyl | H | H | F | methoxy | $NO_2$ | H |
| phenyl | H | methoxy | H | H | F | ethoxy | $NO_2$ | H |
| phenyl | H | ethoxy | H | H | F | propoxy | $NO_2$ | H |
| phenyl | H | propoxy | H | H | Cl | F | $NO_2$ | H |
| methoxy | H | F | H | H | Cl | Cl | $NO_2$ | H |
| methoxy | H | Cl | H | H | Cl | Br | $NO_2$ | H |
| methoxy | H | Br | H | H | Cl | I | $NO_2$ | H |
| methoxy | H | I | H | H | Cl | methyl | $NO_2$ | H |
| methoxy | H | methyl | H | H | Cl | ethyl | $NO_2$ | H |
| methoxy | H | ethyl | H | H | Cl | propyl | $NO_2$ | H |
| methoxy | H | propyl | H | H | Cl | iso-propyl | $NO_2$ | H |
| methoxy | H | iso-propyl | H | H | Cl | butyl | $NO_2$ | H |
| methoxy | H | butyl | H | H | Cl | sec-butyl | $NO_2$ | H |
| methoxy | H | sec-butyl | H | H | Cl | tert-butyl | $NO_2$ | H |
| methoxy | H | tert-butyl | H | H | Cl | $OCF_3$ | $NO_2$ | H |
| methoxy | H | $OCF_3$ | H | H | Cl | $SCF_3$ | $NO_2$ | H |
| methoxy | H | $SCF_3$ | H | H | Cl | $N(CH_3)_2$ | $NO_2$ | H |
| methoxy | H | $N(CH_3)_2$ | H | H | Cl | phenyl | $NO_2$ | H |
| methoxy | H | phenyl | H | H | Cl | methoxy | $NO_2$ | H |
| methoxy | H | methoxy | H | H | Cl | ethoxy | $NO_2$ | H |
| methoxy | H | ethoxy | H | H | Cl | propoxy | $NO_2$ | H |
| methoxy | H | propoxy | H | H | I | F | $NO_2$ | H |
| ethoxy | H | F | H | H | I | Cl | $NO_2$ | H |
| ethoxy | H | Cl | H | H | I | Br | $NO_2$ | H |
| ethoxy | H | Br | H | H | I | I | $NO_2$ | H |
| ethoxy | H | I | H | H | I | methyl | $NO_2$ | H |
| ethoxy | H | methyl | H | H | I | ethyl | $NO_2$ | H |
| ethoxy | H | ethyl | H | H | I | propyl | $NO_2$ | H |
| ethoxy | H | propyl | H | H | I | iso-propyl | $NO_2$ | H |

-continued

| Compound X, wherein Z is C | | | | | Compound X, wherein Z is N | | | |
|---|---|---|---|---|---|---|---|---|
| R$_1$ | R$_2$ | R$_3$ | R$_4$ | R$_5$ | R$_1$ | R$_3$ | R$_4$ | R$_5$ |
| ethoxy | H | iso-propyl | H | H | I | butyl | NO$_2$ | H |
| ethoxy | H | butyl | H | H | I | sec-butyl | NO$_2$ | H |
| ethoxy | H | sec-butyl | H | H | I | tert-butyl | NO$_2$ | H |
| ethoxy | H | tert-butyl | H | H | I | OCF$_3$ | NO$_2$ | H |
| ethoxy | H | OCF$_3$ | H | H | I | SCF$_3$ | NO$_2$ | H |
| ethoxy | H | SCF$_3$ | H | H | I | N(CH$_3$)$_2$ | NO$_2$ | H |
| ethoxy | H | N(CH$_3$)$_2$ | H | H | I | phenyl | NO$_2$ | H |
| ethoxy | H | phenyl | H | H | I | methoxy | NO$_2$ | H |
| ethoxy | H | methoxy | H | H | I | ethoxy | NO$_2$ | H |
| ethoxy | H | ethoxy | H | H | I | propoxy | NO$_2$ | H |
| ethoxy | H | propoxy | H | H | methyl | F | NO$_2$ | H |
| propoxy | H | F | H | H | methyl | Cl | NO$_2$ | H |
| propoxy | H | Cl | H | H | methyl | Br | NO$_2$ | H |
| propoxy | H | Br | H | H | methyl | I | NO$_2$ | H |
| propoxy | H | I | H | H | methyl | methyl | NO$_2$ | H |
| propoxy | H | methyl | H | H | methyl | ethyl | NO$_2$ | H |
| propoxy | H | ethyl | H | H | methyl | propyl | NO$_2$ | H |
| propoxy | H | propyl | H | H | methyl | iso-propyl | NO$_2$ | H |
| propoxy | H | iso-propyl | H | H | methyl | butyl | NO$_2$ | H |
| propoxy | H | butyl | H | H | methyl | sec-butyl | NO$_2$ | H |
| propoxy | H | sec-butyl | H | H | methyl | tert-butyl | NO$_2$ | H |
| propoxy | H | tert-butyl | H | H | methyl | OCF$_3$ | NO$_2$ | H |
| propoxy | H | OCF$_3$ | H | H | methyl | SCF$_3$ | NO$_2$ | H |
| propoxy | H | SCF$_3$ | H | H | methyl | N(CH$_3$)$_2$ | NO$_2$ | H |
| propoxy | H | N(CH$_3$)$_2$ | H | H | methyl | phenyl | NO$_2$ | H |
| propoxy | H | phenyl | H | H | methyl | methoxy | NO$_2$ | H |
| propoxy | H | methoxy | H | H | methyl | ethoxy | NO$_2$ | H |
| propoxy | H | ethoxy | H | H | methyl | propoxy | NO$_2$ | H |
| propoxy | H | propoxy | H | H | ethyl | F | NO$_2$ | H |
| cyclopropoxy | H | cyclopropoxy | H | H | cyclopropoxy | cyclopropoxy | H | H |
| cyclopropoxy | H | H | H | cyclopropoxy | cyclopropoxy | H | NO$_2$ | cyclopropoxy |

TMDOB stands for 4,4,5,5-tetramethyl-1,3,2-dioxaborolanyl.

Preferably, the nitrated compound obtained by the process according to the present invention is selected from the group consisting of the following compounds

| Compound No. | Chemical structure[a] |
|---|---|
| 101 | nitrobenzene |
| 102 | 1-fluoro-4-nitrobenzene |
| 103 | 1-tert-butyl-4-nitrobenzene |
| 104 | 1-methoxy-4-nitrobenzene |
| 105 | 1-methyl-4-nitrobenzene |

-continued
| Compoud No. | Chemical structure[a] |
|---|---|
| 106 | 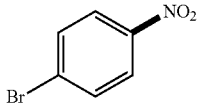 |
| 107 | 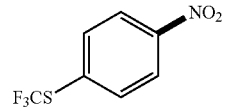 |
| 108 | 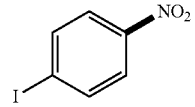 |
| 109 | 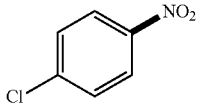 |
| 110 | 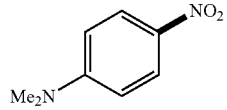 |
| 111 | 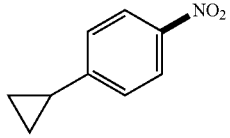 |
| 112 | 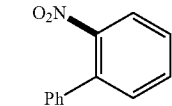 |
| 113 | 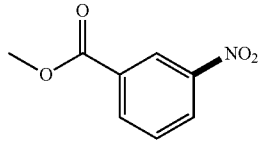 |
| 114 | 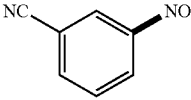 |
| 115 | 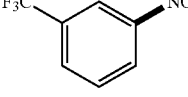 |
| 116 | 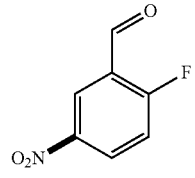 |
| 117 | 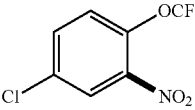 |

-continued
| Compoud No. | Chemical structure[a] |
|---|---|
| 118 | 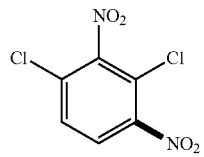 |
| 119 | 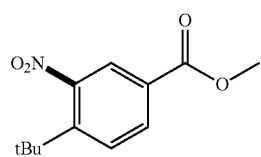 |
| 120 | 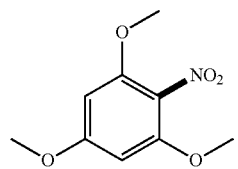 |
| 121 | 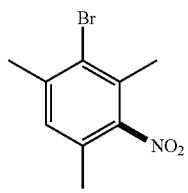 |
| 122 | 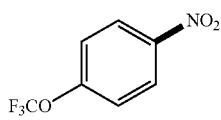 |
| 123 | 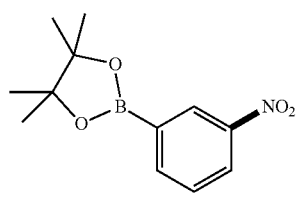 |
| 124 | 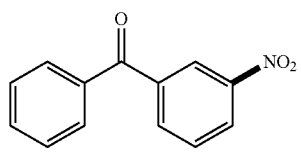 |
| 125 | 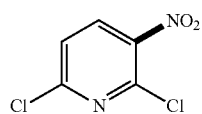 |
| 126 | 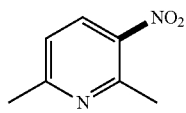 |

-continued

| Compoud No. | Chemical structure[a] |
|---|---|
| 127 | 2,4-dichloro-5-nitropyrimidine |
| 128 | 2,4-dichloro-6-methyl-5-nitropyrimidine |
| 129 | 2-methyl-5-nitroisoindoline-1,3-dione |
| 130 | 1-(2-nitrophenyl)pyrrolidine-2,5-dione |
| 131 | 1-(5-nitrofuran-2-yl)ethan-1-one |
| 132 | 2,2'-dimethoxy-3-nitro-1,1'-binaphthalene |
| 133 | 4-nitro[2.2]paracyclophane |
| 134 | 1-nitronaphthalene |
| 135 | 9-nitroanthracene |

-continued

| Compoud No. | Chemical structure[a] |
|---|---|
| 136 | |
| 137 | |
| 138 | |
| 139 | |
| 140 | |
| 141 | |
| 142 | |
| 143 | |

| Compoud No. | Chemical structure[a] |
|---|---|
| 144 | 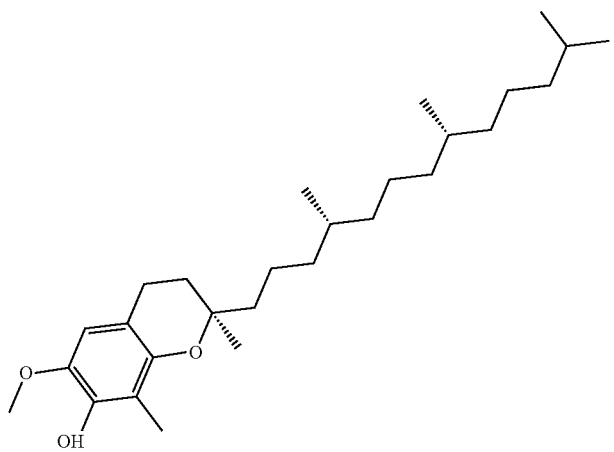 [SMILES: COc1cc2c(c(C)c1O)O[C@](C)(CCC[C@H](C)CCC[C@H](C)CCCC(C)C)CC2] |
| 145 | 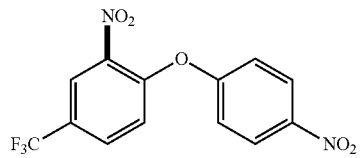 |
| 146 | 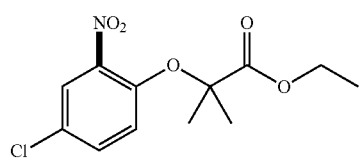 |
| 147 | 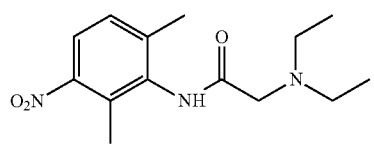 [SMILES: CCN(CC)CC(=O)Nc1c(C)ccc([N+](=O)[O-])c1C] |
| 148 | 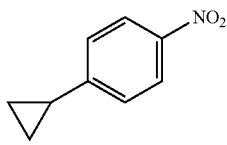 [SMILES: O=[N+]([O-])c1ccc(C2CC2)cc1] |
| 149 | 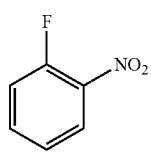 |
| 150 | 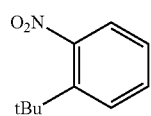 [SMILES: CC(C)(C)c1ccccc1[N+](=O)[O-]] |
| 151 | 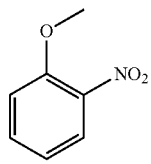 |

-continued

| Compoud No. | Chemical structure[a] |
|---|---|
| 152 | 2-nitrotoluene |
| 153 | 4-nitrobiphenyl |
| 154 | 2-(2-nitrophenyl)-4,4,5,5-tetramethyl-1,3,2-dioxaborolane |
| 155 | 1-nitro-2-(trifluoromethyl)benzene |
| 156 | 1-bromo-2-nitrobenzene |
| 157 | 1-nitro-2-(trifluoromethoxy)benzene |
| 158 | 1-nitro-2-((trifluoromethyl)thio)benzene |
| 159 | 1-(4-nitrophenyl)pyrrolidine-2,5-dione |
| 160 | 1-chloro-2-nitrobenzene |

-continued

| Compoud No. | Chemical structure[a] |
|---|---|
| 161 | 2-(dimethylamino)nitrobenzene (N,N-dimethyl-2-nitroaniline) |
| 162 | 4-nitrobenzophenone |
| 163 | 1-chloro-2-nitro-4-(trifluoromethoxy)benzene |
| 164 | methyl 4-tert-butyl-2-nitrobenzoate |
| 165 | 2-nitrobenzophenone |
| 166 | 1-iodo-2-nitrobenzene |
| 167 | methyl 2-nitrobenzoate |
| 168 | 2-nitro-3-methoxy estrone derivative |
| 169 | 2,4-dinitro-4'-(trifluoromethyl)diphenyl ether |

-continued

| Compoud No. | Chemical structure[a] |
|---|---|
| 170 | 2,6-dihydroxy-3-nitrobenzoic acid |
| 171 | 4-chloro-3-nitrophenol (O2N, OH, Cl substituents) |
| 172 | cyclopropyl(5-nitrothiophen-2-yl)methanone |
| 173 | 5-phenyl-5-(4-nitrophenyl)imidazolidine-2,4-dione + 5-phenyl-5-(2-nitrophenyl)imidazolidine-2,4-dione + 5-phenyl-5-(3-nitrophenyl)imidazolidine-2,4-dione (7.6:4:1) |
| 174 | N-(4-nitro-2-(4-nitrophenoxy)phenyl)methanesulfonamide + N-(4-nitro-2-(2-nitrophenoxy)phenyl)methanesulfonamide (3.3:1) |

-continued

| Compound No. | Chemical structure[a] |
|---|---|
| 175 | 1-(2-methyl-5-nitro-1H-imidazol-1-yl)propan-2-ol structure with Me on imidazole, NO2, and CH2CH(OH)Me substituent |
| 176 | Two isomers: ethyl 1-(4-nitrophenyl)-3-(trifluoromethyl)-1H-pyrazole-4-carboxylate + ethyl 1-(2-nitrophenyl)-3-(trifluoromethyl)-1H-pyrazole-4-carboxylate (8.5:1) |
| 177 | 3-(3,5-dichloro-2-nitrophenyl)-1,5-dimethyl-3-azabicyclo[3.1.0]hexane-2,4-dione |
| 178 | Peracetylated glucopyranoside of 4-acetoxy-2-nitrophenol (OAc groups at 2,3,4,6 positions) |
| 179 | N-(3-nitro-4-hydroxy-5-methoxybenzyl)nonanamide (O2N, HO, OMe on ring; -CH2NHC(O)(CH2)7Me) |
| 180 | (S)-tert-butyl (4-(4-nitrophenyl)-3-oxobutan-2-yl)carbamate + (R)-2-((tert-butoxycarbonyl)amino)-3-(2-nitrophenyl)propanoic acid (3.8:1) |

A further embodiment of the present relates to the use of a compound of formula (I)

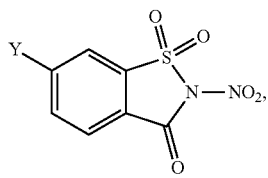

wherein Y is selected from the group consisting of hydrogen and nitro, as nitrating agent of a compound (A) comprising an aromatic or heteroaromatic ring.

EXPERIMENTS

Synthesis of Compound of Formula (Ia)

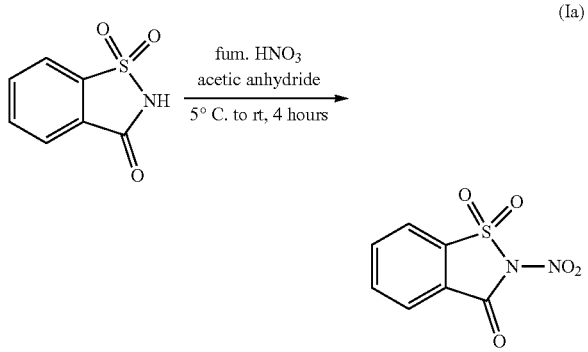

Representative procedure for synthesis of reagent 1: In a 250 mL three necked round bottom flask equipped with dropping funnel, air outlet and stirring bar was placed N-saccharin (10.0 g, 54.64 mmol) in acetic anhydride (25.7 mL, 0.27 mol). The solution was cooled to 0-5° C. with ice-bath and concentrated nitric acid (25.1 mL, 0.61 mol) was added dropwise to the solution during 30 minutes, while dry air being bubbled through the solution rapidly in order to remove excess of nitrogen oxides. N-saccharin was completely dissolved once all nitric acid was added. The cooling bath was removed, and the reaction mixture was stirred at room temperate during at least 4 hours with continuous bubbling of air through the liquid. The precipitate which had formed during the reaction was collected on a sintered glass filter and dried under high vacuum until dryness (11.8 g, 95% yield). The material can be recrystallized from hot chloroform or acetonitrile and is a white crystalline compound. Decomposition temperature: 180-182° C. (mass loss-50%, determined by thermogravimetric analysis, TGA); $^1$H-NMR (300 MHz, CD$_3$CN): δ=8.05 (dt, J=7.4, 1.5 Hz, 1H), 8.14 (dt, J=6.1, 1.4 Hz, 1H), 8.16-8.23 (m, 2H); $^{13}$C-NMR (75 MHz): δ=121.7, 123.1, 126.5, 134.4, 135.9, 137.6, 151.7; IR (ATR, neat): 3097, 1781, 1717, 1601, 1463, 1292, 1176, 1068, 1007, 891, 758, 662, 582, 500; HRMS (EI) m/z calc'd for C$_7$H$_4$N$_2$O$_5$S: [M$^+$] 227.9836, found 227.9842; Anal. calcd. for C$_7$H$_4$N$_2$O$_5$S: C, 36.85, H, 1.77, N, 12.28 found: C, 36.88, H, 1.87, N, 12.41.

Colorless crystals of reagent 1 were obtained by slow evaporation from a saturated solution in chloroform/acetonitrile 1:1.

Synthesis of Compound of Formula (Ib)

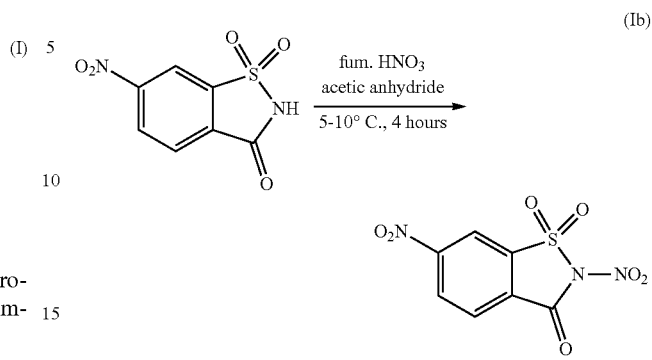

Representative procedure for synthesis of reagent 2: In a 250 mL three necked round bottom flask equipped with dropping funnel, air outlet and stirring bar was placed 6-nitrosaccharin (10.0 g, 36.63 mmol) in acetic anhydride (28.2 mL, 0.30 mol). The solution was cooled 5-10° C. with ice-bath and concentrated nitric acid (28.2 mL, 0.67 mol) was added dropwise to the solution during 30 minutes, while dry air being bubbled through the solution rapidly in order to remove excess of nitrogen oxides.

6-Nitrosaccharin was completely dissolved once all nitric acid was added. The reaction mixture was stirred at 5-10° C. during 4 hours with constant bubbling of dry air through the liquid. The reaction mixture was placed to freezer for 10 hours to complete precipitation of the product. The precipitate was collected on a sintered glass filter, washed with cold chloroform and dried under high vacuum until dryness (9.6 g, 96% yield). The product is a light-yellow (almost white) powder/crystalline compound. Decomposition temperature: 174-176° C. (mass loss~50%, determined by thermogravimetric analysis, TGA); $^1$H-NMR (500 MHz, CD$_3$CN): δ=9.07 (d, J=2.1 Hz, 1H), 8.76 (dd, J=8.5, 2.0 Hz, 1H), 8.43 (d, J=8.4 Hz, 1H); $^{13}$C-NMR (125 MHz, CD$_3$CN): δ=118.3, 127.8, 128.5, 130.6, 135.4, 150.3, 152.9; IR (ATR, neat): 3073, 1732, 1601, 1529, 1424, 1347, 1180, 1064, 1024, 786, 737, 649, 490; Anal. calcd. for C$_7$H$_3$N$_3$O$_7$S C, 30.78, H, 1.11, N, 15.38 found: C, 30.81, H, 1.19, N, 15.50.

Colorless crystals of reagent 2 were obtained by slow evaporation from a saturated solution in chloroform/acetonitrile 1:1.

Nitration of Arenes and Heteroarenes Using Reagent 1

Representative general procedure 1 for nitration of compound A: A 25 mL vessel was charged with reagent 1 (1.3 equiv., 0.65 mmol) and sealed under nitrogen atmosphere. Arene (1.0 equiv., 0.5 mmol) and HFIP (1 mL) were added and the reaction mixture was heated at 55-60° C. for 3 hours. After cooling to room temperature, the solvent was removed in vacuum, and the product was purified by flash column chromatography (SiO$_2$, ethyl acetate/n-hexane gradient).

Representative general procedure 2 for nitration of compound A: A 25 mL vessel was charged with reagent 1 (1.3 equiv., 0.65 mmol), Mg(ClO$_4$)$_2$ (0.05 mmol) and sealed under nitrogen atmosphere. Arene (1.0 equiv., 0.5 mmol) and CH$_3$CN (1 mL) were added and the reaction mixture was heated at 85° C. for 5 hours. After cooling to room temperature, the solvent was removed in vacuum, and the product was purified by flash column chromatography (SiO$_2$, ethyl acetate/n-hexane gradient).

TABLE 1 refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 101 | C6H5-NO2 | >99% | >99% | |
| 102 | 4-F-C6H4-NO2 | 96% | | p:o (1.5:1) |
| 103 | 4-tBu-C6H4-NO2 | 94% | | p:o (9:1) |
| 104 | 4-MeO-C6H4-NO2 | 94% | | p:o (1.85:1) |
| 105 | 4-Me-C6H4-NO2 | 95% | | p:o (1.1:1) |
| 106 | 4-Br-C6H4-NO2 | 92% | | p:o (1.5:1) |
| 107 | 4-F3CS-C6H4-NO2 | 86% (19 h) | 97% | p:o (1.2:1) |
| 108 | 4-I-C6H4-NO2 | 93% | | p:o (2.1:1) |
| 109 | 4-Cl-C6H4-NO2 | 96% | | p:o (1.5:1) |
| 110 | 4-Me2N-C6H4-NO2 | 91% | | p:o (1.5:1) |
| 111 | 4-cyclopropyl-C6H4-NO2 | 97% | | p:o (2.1:1) |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 112 | 2-nitrobiphenyl (O₂N, Ph) | 99% | | o:p (1.5:1) |
| 113 | methyl 3-nitrobenzoate | | 87% | m:o (4:1) |
| 114 | 3-nitrobenzonitrile (NC, NO₂) | 81% (19 h) | 92% | |
| 115 | 1-nitro-3-(trifluoromethyl)benzene (F₃C, NO₂) | 72% (19 h) | 87% | m:o (4.8:1) |
| 116 | 2-fluoro-5-nitrobenzaldehyde | 75% (19 h) | 84% | |
| 117 | 4-chloro-2-nitro-1-(trifluoromethoxy)benzene | 92% (19 h) | 97% | (1:0.6) |
| 118 | 1,3-dichloro-2,4-dinitrobenzene | 37% (19 h) | 72% | |
| 119 | methyl 4-tert-butyl-3-nitrobenzoate | 87% (19 h) | 94% | (2.5:1) |
| 120 | 2-nitro-1,3,5-trimethoxybenzene | | 93% | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 121 | Br-substituted trimethylbenzene with NO2 | 96% | | |
| 122 | F3CO-C6H4-NO2 | 86% (19 h) | 97% (19 h) | p:o (4.6:1) |
| 123 | Pinacol boronate with NO2 | 81% | | m:o (1:0.9) |
| 124 | Benzophenone with NO2 | 98% (19 h) | | o:m:p (0.8:1:0.6) |
| 125 | 2,6-dichloro-3-nitropyridine | | 86% | |
| 126 | 2,6-dimethyl-3-nitropyridine | | 82% | |
| 127 | 2,4-dichloro-5-nitropyrimidine | | 76% | |
| 128 | 2,4-dichloro-6-methyl-5-nitropyrimidine | | 77% | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 129 | | | 86% | |
| 130 | | 94% | 97% | p:o (1:1.1) |
| 131 | | 74% (19 h) | | |
| 132 | | 64% | | |
| 133 | | | 94% | |
| 134 | | 93% | | |
| 135 | | 92% | | |
| 136 | | | 72% | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 137 | | 79% (19 h) | | |
| 138 | | 91% | | (6:1) |
| 139 | | 91% | | |
| 140 | | 85% | | |
| 141 | | 89% (19 h) | | (2.5:1) |
| 142 | | 71% (19 h) | | |
| 143 | | 90% | | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 144 | *(structure)* | 75% | | |
| 145 | *(structure)* | 88% (19 h) | | (15:1) |
| 146 | *(structure)* | 98% | | |
| 147 | *(structure)* | 71% | | |
| 148 | *(structure)* | 65.7% | | |
| 149 | *(structure)* | 19.2% | | |
| 150 | *(structure)* | 9.4% | | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 151 | 2-methoxy-nitrobenzene | 33% | | |
| 152 | 2-methyl-nitrobenzene | 45.3% | | |
| 153 | 4-nitrobiphenyl | 39.6% | | |
| 154 | 2-(nitrophenyl)-pinacol boronate | 38.4% | | |
| 155 | 2-trifluoromethyl-nitrobenzene | 12.2% | | |
| 156 | 2-bromo-nitrobenzene | 36.8 | | |
| 157 | 2-(trifluoromethoxy)-nitrobenzene | 14.8% (19 h) | | |
| 158 | 2-(trifluoromethylthio)-nitrobenzene | 41% (19 h) | | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 159 | 1-(4-nitrophenyl)pyrrolidine-2,5-dione | 42.7% (19 h) | | |
| 160 | 1-chloro-2-nitrobenzene | 38.4% | | |
| 161 | N,N-dimethyl-2-nitroaniline | 36.4% | | |
| 162 | (4-nitrophenyl)(phenyl)methanone | 24.5% (19 h) | | |
| 163 | 1-chloro-4-(trifluoromethoxy)-2-nitrobenzene | 34.5% (19 h) | | |
| 164 | methyl 4-tert-butyl-2-nitrobenzoate | 24.9% (19 h) | | |
| 165 | (2-nitrophenyl)(phenyl)methanone | 32.7% (19 h) | | |
| 166 | 1-iodo-2-nitrobenzene | 30% (19 h) | | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 167 | | | 17.4% | |
| 168 | | | 13% | |
| 169 | | | 5.5% (19 h) | |
| 170 | | | 88% | |
| 171 | | | 93% | |
| 172 | | | 84% (19 H) | |
| 173 | (7.6:4:1) | | 98% | |

TABLE 1-continued
refers to compounds 101 to 146 and indicates the Isolated yield of said compound using general procedure 1 or general procedure 2 (total yield of isomers) and the ratio of isomers.
| Compound No. | Chemical structure[a] | Isolated yield in %[b] using general procedure 1 | Isolated yield in %[b] using general procedure 2 | Ratio of isomers[c] |
|---|---|---|---|---|
| 174 | 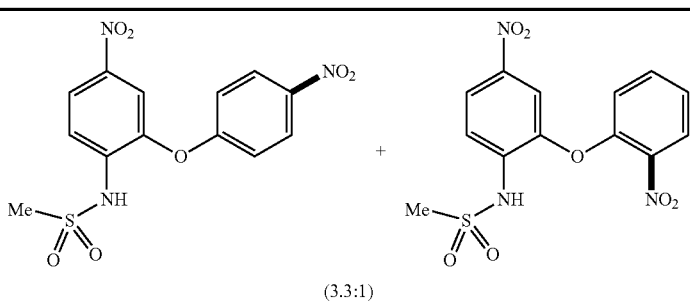 (3.3:1) | 76.1% | | |
| 175 | 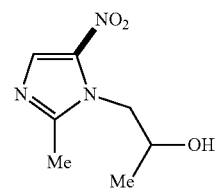 | 44% | | |
| 176 | 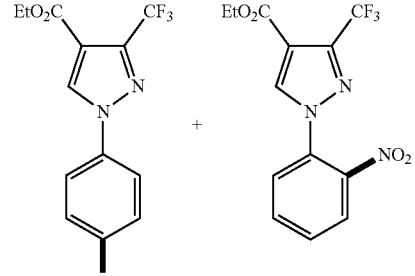 (8.5:1) | 83% | | |
| 177 | 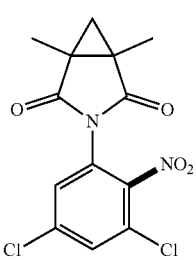 | 91% (19 h) | | |
| 178 | 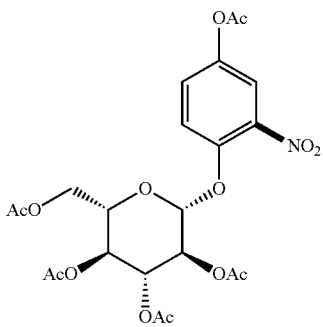 | 74% | | |

TABLE 1-continued refers to compounds 101 to 146 and indicates the Isolated yield of said compound using general procedure 1 or general procedure 2 (total yield of isomers) and the ratio of isomers.

| Compound No. | Chemical structure[a] | Isolated yield in %[b] using general procedure 1 | Isolated yield in %[b] using general procedure 2 | Ratio of isomers[c] |
|---|---|---|---|---|
| 179 | ![structure of compound 179: 3-nitro-4-hydroxy-5-methoxybenzyl nonanamide] | 94% | | |
| 180 | ![structure of compound 180: mixture of Boc-4-nitrophenylalanine and Boc-2-nitrophenylalanine] (3.8:1) | 51% | | |

[a]Major isomer is shown;
[b]The time is extended for some substrates to 19 h in order to complete the reaction. The separated yield of isomers is summarized as a total yield;
[c]The ratio of isomers is shown only for the procedure (1 or 2), which gives the highest yield.

Spectroscopic Data

Nitrobenzene (Compound of Formula 101)

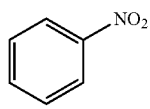

Yield 99% (using the general procedure 1); yield 99% (using the general procedure 2); yellowish oil; $^1$H NMR (300 MHz, Chloroform-d) δ 8.16 (d, J=7.6 Hz, 2H), 7.68 (t, J=7.6 Hz, 1H), 7.52 (m, 2H); $^{13}$C NMR (101 MHz, Chloroform-d) δ 147.88, 134.51, 129.11, 123.24.

1-Fluoro-4-nitrobenzene (Compound of Formula 102)

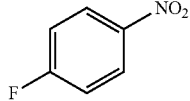

Yield 76.8% (using the general procedure 1); light yellow solid; mp 109-112° C.; $^1$H NMR (300 MHz, Chloroform-d) δ 8.55-8.08 (m, 2H), 7.64-6.86 (m, 2H); $^{13}$C NMR (75 MHz, Chloroform-d) δ 166.30 (d, J=257.9 Hz), 144.43, 126.35 (d, J=10.0 Hz), 116.44 (d, J=23.7 Hz); $^{19}$F NMR (282 MHz, Chloroform-d) δ −102.00.

1-(Tert-butyl)-4-nitrobenzene (Compound of Formula 103)

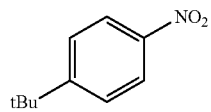

Yield 84.6% (using the general procedure 1); light yellow solid; mp 99-102° C.; $^1$H NMR (300 MHz, Chloroform-d) δ 8.50-7.99 (m, 2H), 7.86-7.34 (m, 2H), 1.36 (s, 9H); $^{13}$C NMR (75 MHz, Chloroform-d) δ 158.88, 145.96, 126.26, 123.37, 35.43, 31.08.

1-Methoxy-4-nitrobenzene (Compound of Formula 104)

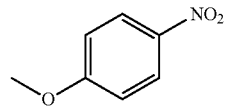

Yield 61% (using the general procedure 1); light yellow solid; mp 52-54° C.; $^1$H NMR (300 MHz, Chloroform-d) δ 8.51-8.08 (m, 2H), 7.21-6.80 (m, 2H), 3.98 (s, 3H); $^{13}$C NMR (75 MHz, Chloroform-d) δ 164.64, 141.61, 125.94, 114.05, 56.00.

1-Methyl-4-nitrobenzene (Compound of Formula 105)

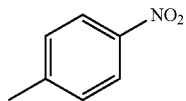

Yield 49.7% (using the general procedure 1); light yellow solid; mp 51-53° C.; $^1$H NMR (300 MHz, Chloroform-d) δ 8.09 (d, J=8.6 Hz, 2H), 7.31 (d, J=7.4 Hz, 2H), 2.45 (s, 3H); $^{13}$C NMR (75 MHz, Chloroform-d) δ 146.19, 145.99, 129.83, 123.53, 21.62.

1-Bromo-4-nitrobenzene (Compound of Formula 106)

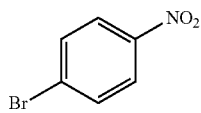

Yield 55.2% (using the general procedure 1); yellow solid; mp 123-125° C.; $^1$H NMR (300 MHz, Chloroform-d) δ 8.10 (d, J=9.0 Hz, 2H), 7.69 (d, J=9.0 Hz, 2H); $^{13}$C NMR (75 MHz, Chloroform-d) δ 147.09, 132.66, 130.00, 125.04.

(4-Nitrophenyl)(trifluoromethyl)sulfane (Compound of Formula 107)

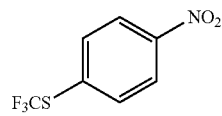

Yield 45% (using the general procedure 1, 19 hours); yield 52.9% (using the general procedure 2); yellowish oil; $^1$H NMR (400 MHz, Chloroform-d) δ 8.40-8.12 (m, 2H), 7.83 (d, J=8.7 Hz, 2H); $^{13}$C NMR (101 MHz, Chloroform-d) δ 149.15, 136.08, 132.56 (q, J=2.0 Hz), 128.94 (q, J=308.8 Hz), 124.35; $^{19}$F NMR (376 MHz, Chloroform-d) δ −41.34.

1-Iodo-4-nitrobenzene (Compound of Formula 108)

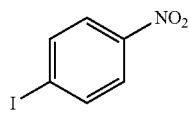

Yield 63% (using the general procedure 1); yellow solid; mp 53-55° C.; $^1$H NMR (300 MHz, Chloroform-d) δ 7.93 (d, J=9.0 Hz, 2H), 7.92 (d, J=9.0 Hz, 2H); $^{13}$C NMR (75 MHz, Chloroform-d) δ 147.83, 138.71, 124.88, 102.68.

1-Chloro-4-nitrobenzene (Compound of Formula 109)

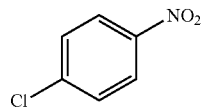

Yield 57.6% (using the general procedure 1); yellowish solid; mp 82-84° C.; $^1$H NMR (300 MHz, Chloroform-d) δ 8.19 (d, J=9.0 Hz, 2H), 7.52 (d, J=9.0 Hz, 2H); $^{13}$C NMR (75 MHz, Chloroform-d) δ 146.60, 141.42, 129.62, 124.97.

N,N-Dimethyl-4-nitroaniline (Compound of Formula 110)

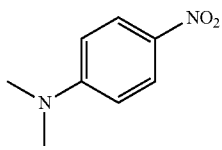

Yield 54.6% (using the general procedure 1); yellow solid; mp 162-164° C.; $^1$H NMR (300 MHz, Chloroform-d) δ 8.10 (d, J=9.4 Hz, 2H), 6.59 (d, J=9.4 Hz, 2H), 3.10 (s, 6H); $^{13}$C NMR (75 MHz, Chloroform-d) δ 154.26, 136.97, 126.12, 110.26, 40.28.

1-Cyclopropyl-2-nitrobenzene (Compound of Formula 111)

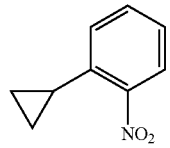

Yield 31.3% (using the general procedure 1); white solid, mp 33-34° C.; $^1$H NMR (300 MHz, Chloroform-d) δ 7.87 (d, J=8.1 Hz, 1H), 7.54 (t, J=7.6 Hz, 1H), 7.43-7.29 (m, 1H), 7.23 (d, J=7.8 Hz, 1H), 2.46 (ddd, J=13.9, 8.5, 5.4 Hz, 1H), 1.23-1.01 (m, 2H), 0.83-0.70 (m, 2H); $^{13}$C NMR (75 MHz, Chloroform-d) δ 151.25, 138.05, 132.57, 127.96, 126.41, 124.08, 12.51, 8.08.

2-Nitro-1,1'-biphenyl (Compound of Formula 112)

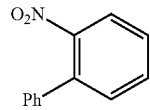

Yield 59.4% (using the general procedure 1); yellow solid; mp 36-38° C.; $^1$H NMR (300 MHz, Chloroform-d) δ 7.86 (d, J=8.0 Hz, 1H), 7.62 (td, J=7.5, 1.1 Hz, 1H), 7.55-7.38 (m, 5H), 7.38-7.29 (m, 2H); $^{13}$C NMR (75 MHz, Chloroform-d) δ 149.39, 137.44, 136.40, 132.29, 132.00, 128.72, 128.27, 128.19, 127.94, 124.10.

Methyl 3-nitrobenzoate (Compound of Formula 113)

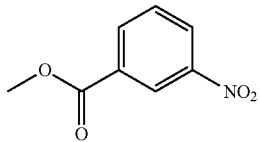

Yield 69.6% (using the general procedure 2); yellow crystalline compound; mp 77-79° C.; $^1$H NMR (300 MHz, Chloroform-d) δ 8.86 (t, J=2.0 Hz, 1H), 8.39 (ddt, J=14.1, 7.8, 1.3 Hz, 2H), 7.65 (t, J=8.0 Hz, 1H), 3.99 (s, 3H); $^{13}$C NMR (75 MHz, Chloroform-d) δ 164.99, 148.34, 135.29, 131.93, 129.66, 127.42, 124.65, 52.83.

3-Nitrobenzonitrile (Compound of Formula 114)

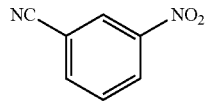 [SMILES: N#Cc1cccc([N+](=O)[O-])c1]

Yield 81% (using the general procedure 1, 19 hours); yield 92% (using the general procedure 2); yellow solid; 115-117° C.; $^1$H NMR (300 MHz, Chloroform-d) δ 8.53 (t, J=1.9 Hz, 1H), 8.48 (ddd, J=8.3, 2.4, 1.2 Hz, 1H), 8.00 (dt, J=7.7, 1.4 Hz, 1H), 7.74 (t, J=8.0 Hz, 1H); $^{13}$C NMR (75 MHz, Chloroform-d) δ 148.30, 137.64, 130.72, 127.57, 127.27, 116.57, 114.19.

1-Nitro-3-(trifluoromethyl)benzene (Compound of Formula 115)

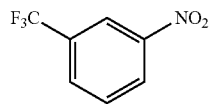

Yield 59.8% (using the general procedure 1, 19 hours); yellow oil; yield 72% (using the general procedure 2); $^1$H NMR (300 MHz, Chloroform-d) δ 8.50 (d, J=1.9 Hz, 1H), 8.44 (dd, J=8.3, 2.2 Hz, 1H), 7.98 (d, J=7.8 Hz, 1H), 7.74 (t, J=8.0 Hz, 1H); $^{13}$C NMR (75 MHz, Chloroform-d) δ 148.33, 132.36 (q, J=34.1 Hz), 131.15 (q, J=3.5 Hz), 130.37, 126.69 (d, J=0.75 Hz), 122.73 (q, J=270.7 Hz), 120.87 (q, J=3.9 Hz); $^{19}$F NMR (282 MHz, Chloroform-d) δ -62.95.

2-Fluoro-5-nitrobenzaldehyde (Compound of Formula 116)

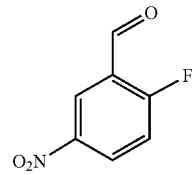 [SMILES: O=Cc1cc([N+](=O)[O-])ccc1F]

Yield 75% (using the general procedure 1, 19 hours); yield 84% (using the general procedure 2); pale-orange solid; mp 58-60° C.; $^1$H NMR (300 MHz, Chloroform-d) δ 10.37 (s, 1H), 8.74 (dd, J=5.9, 2.9 Hz, 1H), 8.49 (ddd, J=9.0, 4.4, 2.9 Hz, 1H), 7.40 (t, J=9.0 Hz, 1H); $^{13}$C NMR (75 MHz, Chloroform-d) δ 184.84 (d, J=5.9 Hz), 167.30 (d, J=268.4 Hz), 144.86, 131.05 (d, J=11.0 Hz), 124.95 (d, J=4.1 Hz), 124.63 (d, J=10.5 Hz), 118.33 (d, J=23.2 Hz); $^{19}$F NMR (282 MHz, Chloroform-d) δ -111.19 (dt, J=9.9, 5.2 Hz); IR (ATR, neat): 3076, 2899, 1693, 1619, 1523, 1470, 1346, 1226, 1070, 934, 744, 547.

4-Chloro-2-nitro-1-(trifluoromethoxy)benzene (Compound of Formula 117)

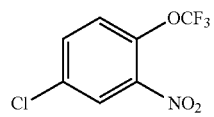 [SMILES: O=[N+]([O-])c1cc(Cl)ccc1OC(F)(F)F]

Yield 57.5% (using the general procedure 1, 19 hours); colorless oil; yield 60.6% (using the general procedure 2); $^1$H NMR (500 MHz, Chloroform-d) δ 7.99 (d, J=2.5 Hz, 1H), 7.64 (dd, J=8.9, 2.6 Hz, 1H), 7.42 (dq, J=8.8, 1.4 Hz, 1H); $^{13}$C NMR (126 MHz, Chloroform-d) δ 142.96, 139.83, 134.22, 133.38, 126.06, 124.50, 120.08 (q, J=261.4 Hz); $^{19}$F NMR (471 MHz, Chloroform-d) δ -57.75.

1,3-Dichloro-2,4-dinitrobenzene (Compound of Formula 118)

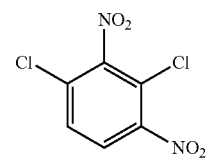 [SMILES: O=[N+]([O-])c1ccc(Cl)c([N+](=O)[O-])c1Cl]

Yield 37% (using the general procedure 1, 19 hours); yield 79% (using the general procedure 2); yellow solid; mp 70-72° C.; $^1$H NMR (400 MHz, Chloroform-d) δ 8.03 (dd, J=8.9, 1.0 Hz, 1H), 7.65 (dd, J=8.9, 1.0 Hz, 1H); $^{13}$C NMR (101 MHz, Chloroform-d) δ 149.49, 146.68, 130.94, 129.54, 126.75, 121.51.

Methyl 4-(tert-butyl)-3-nitrobenzoate (Compound of Formula 119)

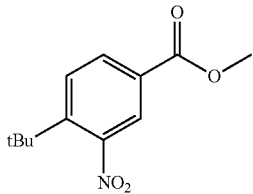 [SMILES: COC(=O)c1ccc(C(C)(C)C)c([N+](=O)[O-])c1]

Yield 62.1% (using the general procedure 1, 19 hours); yellow oil; yield 67.2% (using the general procedure 2); $^1$H NMR (400 MHz, Chloroform-d) δ 8.07 (dd, J=8.4, 1.9 Hz, 1H), 7.97 (d, J=1.9 Hz, 1H), 7.64 (d, J=8.4 Hz, 1H), 3.93 (s, 3H), 1.42 (s, 9H); $^{13}$C NMR (101 MHz, Chloroform-d) δ 164.91, 151.09, 146.21, 131.36, 129.13, 129.02, 125.06, 52.55, 36.12, 30.51.

1,3,5-Trimethoxy-2-nitrobenzene (Compound of Formula 120)

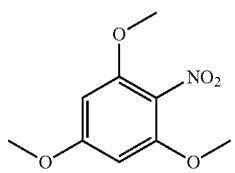

Yield 93% (using the general procedure 1); yellow crystalline compound; mp 151-153° C.; $^1$H NMR (300 MHz, Chloroform-d) δ 6.11 (s, 2H), 3.85 (s, 6H), 3.83 (s, 3H); $^{13}$C NMR (75 MHz, Chloroform-d) δ 162.21, 153.36, 126.56, 90.82, 56.44, 55.75.

2-Bromo-1,3,5-trimethyl-4-nitrobenzene (Compound of Formula 121)

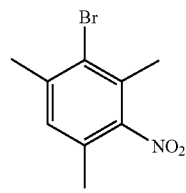

Yield 96% (using the general procedure 1); yellow solid; mp 58-62° C.; $^1$H NMR (300 MHz, Chloroform-d) δ 7.10 (s, 1H), 2.49 (s, 3H), 2.43 (s, 3H), 2.29 (s, 3H); $^{13}$C NMR (75 MHz, Chloroform-d) δ 150.66, 140.61, 130.35, 129.62, 127.67, 125.47, 24.04, 18.95, 17.03.

1-Nitro-4-(trifluoromethoxy)benzene (Compound of Formula 122)

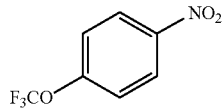 [SMILES: O=[N+]([O-])c1ccc(OC(F)(F)F)cc1]

Yield 71.2% (using the general procedure 1, 19 hours); yellowish oil; yield 79.7% (using the general procedure 2, 19 hours); $^1$H NMR (300 MHz, Chloroform-d) δ 8.59-8.02 (m, 2H), 7.64-7.27 (m, 2H); $^{13}$C NMR (75 MHz, Chloroform-d) δ 153.67 (q, J=1.6 Hz), 146.02, 125.85, 121.00, 120.20 (q, J=258.7 Hz); $^{19}$F NMR (282 MHz, Chloroform-d) δ -57.81.

4,4,5,5-Tetramethyl-2-(3-nitrophenyl)-1,3,2-dioxaborolane (Compound of Formula 123)

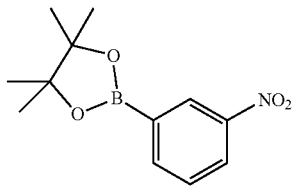 [SMILES: CC1(C)OB(c2cccc([N+](=O)[O-])c2)OC1(C)C]

Yield 42.6% (using the general procedure 1); yellow solid; mp 73-74° C.; $^1$H NMR (300 MHz, Chloroform-d) δ 8.73-8.55 (m, 1H), 8.33-8.24 (m, 1H), 8.09 (d, J=7.3 Hz, 1H), 7.53 (t, J=7.8 Hz, 1H), 1.36 (s, 12H); $^{13}$C NMR (75 MHz, Chloroform-d) δ 147.90, 140.67, 129.43, 128.76, 125.87, 84.63, 24.91.

(3-Nitrophenyl)(phenyl)methanone (Compound of Formula 124)

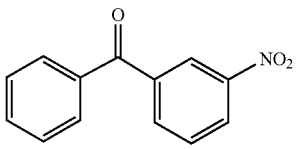 [SMILES: O=C(c1ccccc1)c1cccc([N+](=O)[O-])c1]

Yield 40.8% (using the general procedure 1, 19 hours); light yellow solid; mp 94-96° C.; $^1$H NMR (400 MHz, Chloroform-d) δ 8.62 (t, J=1.8 Hz, 1H), 8.45 (ddd, J=8.2, 2.2, 1.0 Hz, 1H), 8.14 (dt, J=7.6, 1.2 Hz, 1H), 7.87-7.76 (m, 2H), 7.71 (t, J=7.9 Hz, 1H), 7.66 (t, J=7.4 Hz, 1H), 7.53 (t, J=7.7 Hz, 2H), $^{13}$C NMR (101 MHz, Chloroform-d) δ 194.16, 148.09, 139.07, 136.26, 135.44, 133.37, 130.01, 129.64, 128.74, 126.72, 124.72.

2,6-Dichloro-3-nitropyridine (Compound of Formula 125)

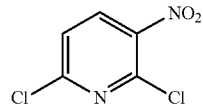 [SMILES: O=[N+]([O-])c1ccc(Cl)nc1Cl]

Yield 86% (using the general procedure 2); yellow solid; mp 53-55° C.; $^1$H NMR (300 MHz, Acetonitrile-$d_3$) δ 8.36 (d, J=8.4 Hz, 1H), 7.63 (d, J=8.5 Hz, 1H); $^{13}$C NMR (75 MHz, Acetonitrile-$d_3$) δ 152.38, 143.54, 142.06, 137.28, 124.26, 116.91.

2,6-Dimethyl-3-nitropyridine (Compound of Formula 126)

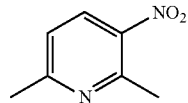

Yield 82% (using the general procedure 2); yellow solid; mp 36-38° C.; $^1$H NMR (300 MHz, Chloroform-d) δ 8.15 (d, J=8.3 Hz, 1H), 7.14 (d, J=8.3 Hz, 1H), 2.80 (s, 3H), 2.59 (s, 3H); $^{13}$C NMR (75 MHz, Chloroform-d) δ 163.02, 153.32, 143.69, 132.87, 121.42, 24.71, 24.06.

2,4-Dichloro-5-nitropyrimidine (Compound of Formula 127)

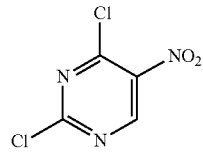 [SMILES: O=[N+]([O-])c1cnc(Cl)nc1Cl]

Yield 76% (using the general procedure 2); yellow solid; 30-32° C.; $^1$H NMR (400 MHz, Acetonitrile-$d_3$) δ 9.25 (s, 1H); $^{13}$C NMR (101 MHz, Acetonitrile-$d_3$) δ 161.68, 157.53, 155.17, 142.15.

2,4-Dichloro-6-methyl-5-nitropyrimidine (Compound of Formula 128)

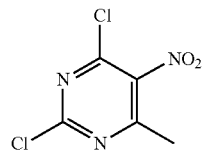

Yield 77% (using the general procedure 2); yellow solid; mp 50-52° C.; $^1$H NMR (300 MHz, Acetonitrile-$d_3$) δ 2.59 (d, J=1.0 Hz, 3H); $^{13}$C NMR (75 MHz, Acetonitrile-$d_3$) δ 164.68, 158.52, 152.68, 143.23.

2-Methyl-5-nitroisoindoline-1,3-dione (Compound of Formula 129)

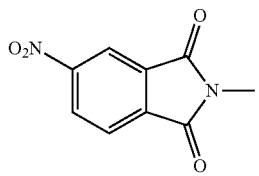

Yield 86% (using the general procedure 2); yellow solid; mp 179-180° C.; $^1$H NMR (300 MHz, Acetonitrile-$d_3$) δ 8.58 (dd, J=8.1, 1.9 Hz, 1H), 8.53 (d, J=2.0 Hz, 1H), 8.03 (d, J=8.1 Hz, 1H), 3.15 (s, 3H); $^{13}$C NMR (75 MHz, Acetonitrile-$d_3$) δ 166.24, 165.99, 151.50, 136.59, 133.41, 129.01, 123.78, 117.58, 23.44.

1-(2-Nitrophenyl)pyrrolidine-2,5-dione (Compound of Formula 130)

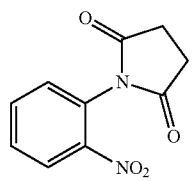 [SMILES: O=C1CCC(=O)N1c1ccccc1[N+](=O)[O-]]

Yield 51.3% (using the general procedure 1, 19 hours); yield 51% (using the general procedure 2); yellow solid; mp 157-158° C.; $^1$H NMR (300 MHz, Chloroform-d) δ 8.18 (d, J=8.2 Hz, 1H), 7.76 (t, J=7.7 Hz, 1H), 7.61 (t, J=7.9 Hz, 1H), 7.39 (d, J=7.9 Hz, 1H), 2.98 (d, J=15 Hz, 2H), 2.92 (d, J=15 Hz, 2H); $^{13}$C NMR (75 MHz, Chloroform-d) δ 175.42, 145.29, 134.45, 130.57, 130.23, 126.17, 126.02, 28.90.

1-(5-Nitrofuran-2-yl)ethan-1-one (Compound of Formula 131)

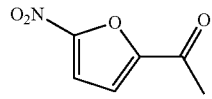

Yield 77% (using the general procedure 1); yellow solid; mp 78-79° C.; $^1$H NMR (300 MHz, Chloroform-d) δ 7.30 (d, J=3.8 Hz, 1H), 7.20 (d, J=3.8 Hz, 1H), 2.54 (s, 3H); $^{13}$C NMR (75 MHz, Chloroform-d) δ 186.76, 151.95, 151.55, 116.75, 111.93, 26.32.

(R)-2,2'-dimethoxy-3-nitro-1,1'-binaphthalene (Compound of Formula 132)

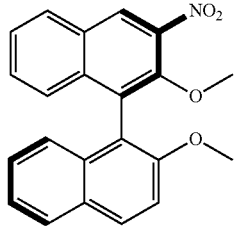

Yield 64% (using the general procedure 1); yellow solid; mp 189-191° C.; $^1$H NMR (300 MHz, Chloroform-d) δ 8.77 (d, J=2.3 Hz, 1H), 8.10 (d, J=9.1 Hz, 1H), 7.94 (d, J=9.1 Hz, 1H), 7.87 (dd, J=9.4, 2.3 Hz, 1H), 7.82 (d, J=8.2 Hz, 1H), 7.52 (d, J=9.0 Hz, 1H), 7.39 (d, J=9.0 Hz, 1H), 7.27 (ddd, J=8.1, 6.8, 1.3 Hz, 1H), 7.19-7.09 (m, 2H), 6.95 (d, J=8.5 Hz, 1H), 3.75 (s, 3H), 3.70 (s, 3H); $^{13}$C NMR (75 MHz, Chloroform-d) δ 158.16, 154.95, 143.78, 136.94, 133.68, 131.87, 130.12, 129.23, 128.21, 127.25, 126.78, 126.74, 125.18, 124.65, 123.77, 120.13, 119.75, 117.95, 115.53, 113.89, 56.75, 56.64; IR (ATR, neat): 3062, 2934, 1616, 1509, 1462, 1334, 1265, 1149, 1060, 828, 743, 595; HRMS (ESI+) calcd (m/z) for $C_{22}H_{18}NO_4$: [M+] 360.1225; found 360.1230.

1²-Nitro-1,4(1,4)-dibenzenacyclohexaphane (Compound of Formula 133)

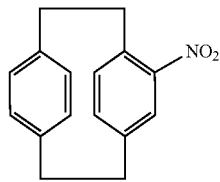 [SMILES: O=[N+]([O-])c1cc2ccc1CCc1ccc(cc1)CC2]

Yield 94% (using the general procedure 2); yellow solid; mp 155-157° C. $^1$H NMR (500 MHz, Chloroform-d) δ 7.22 (d, J=1.9 Hz, 1H), 6.79 (dd, J=7.8, 1.9 Hz, 1H), 6.66-6.60 (m, 2H), 6.57 (qd, J=7.9, 1.9 Hz, 2H), 6.51-6.45 (m, 1H), 4.03 (ddd, J=13.3, 9.5, 2.0 Hz, 1H), 3.19 (tdt, J=12.8, 7.2, 3.1 Hz, 4H), 3.12-3.02 (m, 2H), 2.90 (ddd, J=13.3, 10.0, 7.1 Hz, 1H); $^{13}$C NMR (126 MHz, Chloroform-d) δ 149.32, 142.08, 139.80, 139.32, 137.77, 137.35, 136.48, 133.20, 133.13, 132.42, 129.99, 129.57, 36.03, 35.01, 34.83, 34.47; IR (ATR, neat): 2924, 1602, 1516, 1482, 1330, 1180, 1094, 903, 804, 634, 507.

Colorless crystals of 1²-nitro-1,4(1,4)-dibenzenacyclohexaphane were obtained by slow evaporation from a saturated solution in ethyl acetate/hexane 1:1.

The crystal structure is shown in FIG. 1.

Crystal data and structure refinement of 1²-nitro-1,4(1,4)-dibenzenacyclohexaphane:

| | |
|---|---|
| Empirical formula | $C_{16}H_{15}NO_2$ |
| Formula weight | 253.29 |
| Temperature/K | 100.0 |
| Crystal system | Monoclinic |
| Space group IT number | 9 |
| Space group name | C 1 c 1 |
| a/Å | 14.308(3) |
| b/Å | 7.3956(16) |
| c/Å | 11.575(2) |
| α/° | 90.0 |
| β/° | 91.230(3) |
| γ/° | 90.0 |
| Volume/Å³ | 1224.6(4) |
| Z | 4 |
| $\rho_{calc}$g/cm³ | 1.374 |
| μ/mm⁻¹ | 0.091 |
| F(000) | 536.0 |
| Crystal size/mm³ | 0.18 × 0.28 × 0.42 |
| Radiation | MoKα (λ = 0.71073) |
| 2Θ range for data collection/° | 2.848 to 26.989 |
| Index ranges | −9 ≤ h ≤ 9, −14 ≤ k ≤ 14, −17 ≤ l ≤ 18 |
| Reflections collected | 6274 |
| Independent reflections | 2612 |
| Data/restraints/parameters | 173/0/2612 |
| Goodness-of-fit on F² | 1.056 |
| Final R indexes [I >= 2σ (I)] | $R_1$ = 0.0659, $wR_2$ = 0.1308 |
| Final R indexes [all data] | $R_1$ = 0.0504, $wR_2$ = 0.1450 |
| Largest diff. peak/hole/e Å⁻³ | 0.418/−0.231 |

1-Nitronaphthalene (Compound of Formula 134)

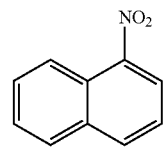 [SMILES: O=[N+]([O-])c1cccc2ccccc12]

Yield 94% (using the general procedure 1); light yellow solid, mp 56-59° C.; $^1$H NMR (300 MHz, Chloroform-d) δ 8.57 (d, J=8.7 Hz, 1H), 8.24 (d, J=7.6 Hz, 1H), 8.12 (d, J=8.2 Hz, 1H), 7.96 (d, J=8.2 Hz, 1H), 7.73 (ddd, J=8.6, 6.9, 1.5 Hz, 1H), 7.63 (t, J=7.5 Hz, 1H), 7.55 (t, J=7.9 Hz, 1H); $^{13}$C NMR (75 MHz, Chloroform-d) δ 134.68, 134.40, 129.49, 128.64, 127.39, 125.19, 124.18, 124.03, 123.18.

9-Nitroanthracene (Compound of Formula 135)

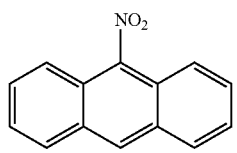 [SMILES: O=[N+]([O-])c1c2ccccc2cc2ccccc12]

Yield 92% (using the general procedure 1); yellow solid, mp 145-147° C.; $^1$H NMR (300 MHz, Chloroform-d) δ 8.55 (s, 1H), 8.02 (d, J=8.4 Hz, 2H), 7.93 (dd, J=8.8, 1.1 Hz, 2H), 7.62 (ddd, J=8.7, 6.7, 1.3 Hz, 2H), 7.52 (ddd, J=8.0, 6.7, 1.1 Hz, 2H); $^{13}$C NMR (75 MHz, Chloroform-d) δ 144.30, 130.80, 130.39, 128.89, 128.41, 126.21, 122.68, 121.40.

1-Chloro-4-((4-chlorophenyl)sulfonyl)-2-nitrobenzene (Compound of Formula 136)

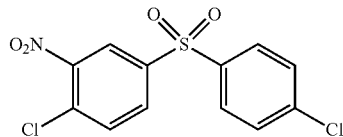 [SMILES: O=[N+]([O-])c1cc(S(=O)(=O)c2ccc(Cl)cc2)ccc1Cl]

Yield 72% (using the general procedure 2); white solid; mp 59-61° C.; $^1$H NMR (400 MHz, DMSO-$d_6$) δ 8.68 (d, J=2.2 Hz, 1H), 8.26 (dd, J=8.5, 2.3 Hz, 1H), 8.10-8.00 (m, 3H), 7.78-7.71 (m, 2H); $^{13}$C NMR (101 MHz, DMSO-$d_6$) δ 148.39, 141.05, 140.20, 138.79, 134.06, 132.62, 131.42, 130.61, 130.37, 125.39.

5,6-Dimethoxy-7-nitro-2,3-dihydro-1H-inden-1-one (Compound of Formula 137)

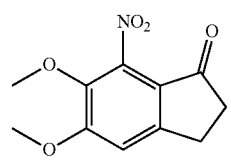 [SMILES: COc1cc2c(c([N+](=O)[O-])c1OC)C(=O)CC2]

Yield 79% (using the general procedure 1, 19 hours); yellow solid; mp 146-148° C.; $^1$H NMR (400 MHz, Chloroform-d) δ 7.03 (s, 1H), 4.00 (s, 3H), 3.90 (s, 3H), 3.29-2.96 (m, 2H), 2.90-2.56 (m, 2H); $^{13}$C NMR (101 MHz, Chloroform-d) δ 200.25, 159.33, 152.87, 140.46, 139.90, 120.46, 110.20, 62.50, 56.88, 36.81, 25.90.

(13S)-3-Methoxy-13-methyl-4-nitro-6,7,8,9,11,12,13,14,15,16-decahydro-17H-cyclopenta[a]phenanthren-17-one (Compound of Formula 138)

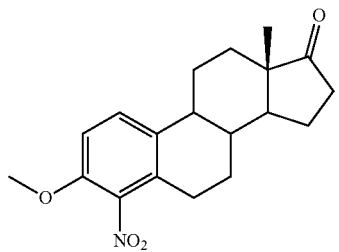 [SMILES: COc1ccc2c(c1[N+](=O)[O-])CCC1C2CC[C@]2(C)C(=O)CCC12]

Yield 78% (using the general procedure 1); yellow solid; mp 150-152° C.; $^1$H NMR (500 MHz, Chloroform-d) δ 7.34 (d, J=8.8 Hz, 1H), 6.85 (d, J=8.8 Hz, 1H), 3.86 (s, 3H), 2.86-2.69 (m, 2H), 2.51 (dd, J=19.1, 8.8 Hz, 1H), 2.42-2.35 (m, 1H), 2.30-2.21 (m, 1H), 2.15 (dt, J=18.6, 8.9 Hz, 1H), 2.09-2.00 (m, 2H), 1.97 (dd, J=9.1, 2.6 Hz, 1H), 1.68-1.36 (m, 6H), 0.91 (s, 3H); $^{13}$C NMR (126 MHz, Chloroform-d) δ 148.55, 141.67, 133.20, 128.86, 127.63, 109.91, 56.32, 50.16, 47.83, 43.83, 41.54, 37.52, 35.80, 31.44, 25.96, 25.44, 23.92, 21.52, 13.81; IR (ATR, neat): 2929, 1729, 1619, 1514, 1450, 1267, 1014, 755; HRMS (ESI+) calcd (m/z) for $C_{19}H_{23}NO_4$: [M−Na$^+$] 352.1515; found 352.1519.

3,4-Dimethoxy-5-nitrobenzaldehyde (Compound of Formula 139)

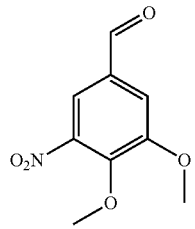

Yield 91% (using the general procedure 1); light yellow solid; mp 61-62° C.; $^1$H NMR (300 MHz, Chloroform-d) δ 10.46 (s, 1H), 7.62 (s, 1H), 7.43 (s, 1H), 4.04 (s, 3H), 4.03 (s, 3H); $^{13}$C NMR (75 MHz, Chloroform-d) δ 187.81, 153.39, 152.58, 144.05, 125.72, 109.95, 107.35, 56.95, 56.89; HRMS (EI) calcd (m/z) for $C_9H_9NO_5$: [M$^+$] 211.04752; found 211.04744.

(1r,1's,4R,4'R)-4-(3,4-Difluoro-2-nitrophenyl)-4'-propyl-1,1'-bi(cyclohexane) (Compound of Formula 140)

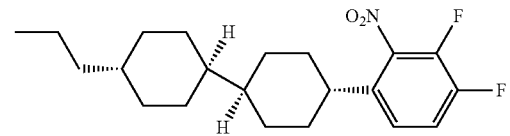 [SMILES: CCC[C@H]1CC[C@H]([C@H]2CC[C@H](c3ccc(F)c(F)c3[N+](=O)[O-])CC2)CC1]

Yield 90% (using the general procedure 1); yellow solid; mp 67-69° C. $^1$H NMR (300 MHz, Chloroform-d) δ 7.66 (dd, J=9.6, 7.3 Hz, 1H), 7.24 (dd, J=11.3, 7.6 Hz, 1H), 3.03 (t, J=11.8 Hz, 1H), 1.97-1.68 (m, 9H), 1.47-0.78 (m, 20H); $^{13}$C NMR (75 MHz, Chloroform-d) δ 152.76 (dd, J=256.7, 12.4 Hz), 147.48 (dd, J=252.0, 14.1 Hz), 145.42-144.20 (m), 140.15 (dd, J=6.2, 4.1 Hz), 116.76 (d, J=19.1 Hz), 114.27 (dd, J=21.3, 1.9 Hz), 43.28, 42.88, 39.82, 38.95, 37.64, 34.15, 33.57, 30.10, 29.99, 20.08, 14.45; $^{19}$F NMR (282 MHz, Chloroform-d) δ −128.75−−128.94 (m), −137.26 (ddd, J=21.7, 9.7, 7.7 Hz); IR (ATR, neat): 2916, 2847, 1600, 1529, 1508, 1445, 1356, 1298, 1186, 882, 804, 633; HRMS (EI) calcd (m/z) for $C_{21}H_{28}NOF_2$: [M$^+$] 348.21335; found 348.21286.

Methyl 2-(4-isobutyl-3-nitrophenyl)propanoate and methyl 2-(4-isobutyl-2-nitrophenyl)propanoate (Compound of Formula 141)

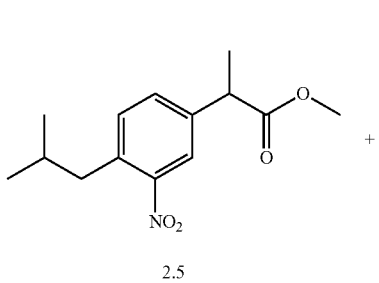

2.5

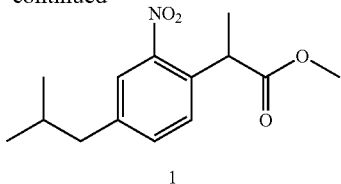

Total yield of two compounds 89% (using the general procedure 1, 19 hours); yellow oil; $^1$H NMR (400 MHz, Chloroform-d) δ 7.80 (d, J=1.9 Hz, 2.5H), 7.70 (s, 1H), 7.44 (dd, J=8.0, 2.0 Hz, 2.5H), 7.36 (d, J=1.1 Hz, 2H), 7.25 (d, J=7.9 Hz, 2.5H), 4.28 (q, J=7.2 Hz, 1H), 3.77 (q, J=7.2 Hz, 2.5H), 3.68 (s, 7.5H), 3.66 (s, 3H), 2.75 (d, J=7.1 Hz, 5H), 2.53 (d, J=7.2 Hz, 2H), 1.89 (dt, J=13.5, 6.8 Hz, 3.5H), 1.58 (d, J=7.2 Hz, 3H), 1.53 (d, J=7.3 Hz, 7.5H), 0.91 (dd, J=6.6, 4.7 Hz, 21H); $^{13}$C NMR (101 MHz, Chloroform-d) δ 174.13, 173.93, 149.91, 148.89, 142.40, 139.78, 135.29, 134.15, 133.05, 132.54, 131.60, 129.48, 125.22, 123.83, 52.42, 52.34, 44.75, 44.58, 41.52, 41.02, 30.08, 29.58, 22.57, 22.36, 18.47, 18.05. IR (ATR, neat): 2956, 1735, 1527, 1347, 1192, 1166, 1066, 854, 818, 678; HRMS (ESI+) calcd (m/z) for $C_{14}H_{19}NNaO_4$: [M–Na$^+$] 288.1200; found 288.1206.

(S)-2-(6-Methoxy-5-nitronaphthalen-2-Yl)propanoic acid (Compound of Formula 143)

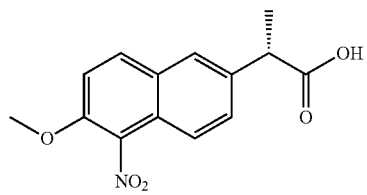 [SMILES: COc1ccc2cc([C@H](C)C(=O)O)ccc2c1[N+](=O)[O-]]

Yield 90% (using the general procedure 1); yellow solid; mp 132-134° C. $^1$H NMR (400 MHz, DMSO-d$_6$) δ 12.42 (s, 1H), 8.22 (d, J=9.2 Hz, 1H), 7.95 (d, J=1.7 Hz, 1H), 7.69 (d, J=9.2 Hz, 1H), 7.64 (dd, J=8.8, 1.8 Hz, 1H), 7.56 (d, J=8.8 Hz, 1H), 4.04 (s, 3H), 3.88 (q, J=7.1 Hz, 1H), 1.47 (d, J=7.1 Hz, 3H); $^{13}$C NMR (101 MHz, DMSO-d$_6$) δ 175.50, 148.61, 138.64, 135.26, 132.94, 130.14, 128.15, 126.80, 124.04, 120.23, 114.82, 57.69, 44.88, 18.65; IR (ATR, neat): 2945, 1722, 1608, 1518, 1359, 1281, 1214, 1163, 1076, 903, 818, 641; HRMS (ESI+) calcd (m/z) for $C_{14}H_{14}NO_5$: [M$^+$] 276.0868; found 276.0866.

(R)-6-Methoxy-2,8-dimethyl-7-nitro-2-((4R,8R)-4,8,12-trimethyltridecyl)chromane (Compound of Formula 144)

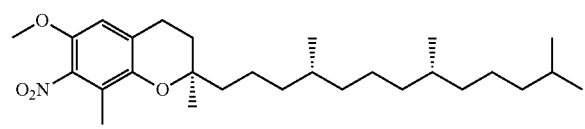 [SMILES: COc1cc2c(c(C)c1[N+](=O)[O-])O[C@](C)(CCC[C@H](C)CCC[C@H](C)CCCC(C)C)CC2]

Yield 75% (using the general procedure 1); yellow oil; $^1$H NMR (300 MHz, Chloroform-d) δ 6.71 (s, 1H), 3.82 (s, 3H), 2.68 (t, J=6.9 Hz, 2H), 2.19 (s, 3H), 1.77 (h, J=7.0 Hz, 2H), 1.56-1.11 (m, 24H), 0.88-0.85 (m, 12H); $^{13}$C NMR (75 MHz, Chloroform-d) δ 145.45, 143.29, 138.88, 129.66, 113.65, 113.16, 75.93, 56.75, 39.46, 39.11, 37.17, 37.14, 37.09, 37.02, 32.53, 32.41, 29.87, 27.71, 24.53, 24.18, 23.60, 22.45, 22.35, 20.64, 19.48, 19.35, 18.07, 16.34; IR (ATR, neat): 2924, 1529, 1476, 1375, 1239, 1102, 1016, 911, 809; HRMS (ESI+) calcd (m/z) for $C_{28}H_{47}NO_4$: [M$^+$] 461.3500; found 461.3500.

2-Nitro-1-(4-nitrophenoxy)-4-(trifluoromethyl)benzene (Fluorodifen) (Compound of Formula 145)

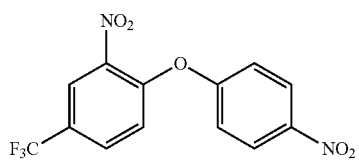 [SMILES: O=[N+]([O-])c1ccc(Oc2ccc(C(F)(F)F)cc2[N+](=O)[O-])cc1]

Yield 82.5% (using the general procedure 1, 19 hours); yellow solid; mp 94-96° C. $^1$H NMR (300 MHz, Chloroform-d) δ 8.39-8.23 (m, 3H), 7.89 (dd, J=8.8, 2.2 Hz, 1H), 7.30 (d, J=8.7 Hz, 1H), 7.20-7.08 (m, 2H); $^{13}$C NMR (126 MHz, Chloroform-d) δ 160.62, 151.06, 144.53, 141.82, 133.97-130.25 (m), 128.06 (q, J=34.8 Hz), 126.44, 124.11 (q, J=3.7 Hz), 123.00, 122.48 (q, J=273.3 Hz), 118.53; $^{19}$F NMR (282 MHz, Chloroform-d) 5-62.47; IR (ATR, neat): 2916, 1600, 1586, 1533, 1347, 1322, 1230, 902, 804, 747, 633; HRMS (EI) calcd (m/z) for $C_{13}H_7N_2F_3O_5$: [M$^+$] 328.03016; found 328.03004.

Colorless crystals of 2-nitro-1-(4-nitrophenoxy)-4-(trifluoromethyl)benzene were obtained by slow evaporation from a saturated solution in ethyl acetate/hexane 1:1.

Figure 2:
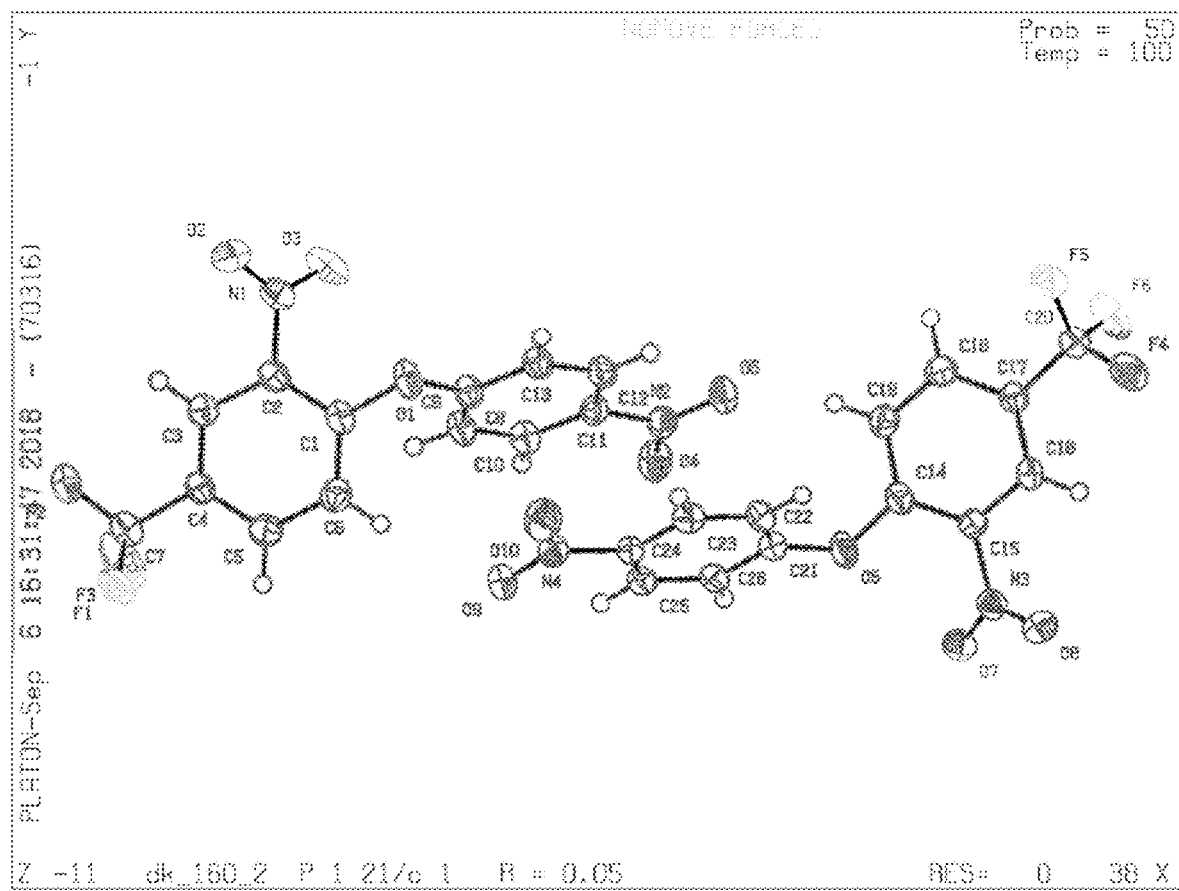
FIG. 2 shows the crystal structure of another exemplary compound.

The crystal structure is shown in FIG. 2.

Crystal data and structure refinement of 2-Nitro-1-(4-nitrophenoxy)-4-(trifluoromethyl)benzene:

| Empirical formula | $C_{13}H_7N_2O_5F_3$ |
| --- | --- |
| Formula weight | 328.21 |
| Temperature/K | 100.0 |
| Crystal system | Monoclinic |
| Space group IT number | 15 |
| Space group name | P 1 21/c 1 |
| a/Å | 21.4056(18) |
| b/Å | 12.0113(10) |
| c/Å | 10.2695(9) |
| α/° | 90.0 |
| β/° | 91.143(2) |
| γ/° | 90.0 |
| Volume/Å$^3$ | 2639.9(4) |
| Z | 8 |
| ρ$_{calc}$g/cm$^3$ | 1.652 |
| μ/mm$^{-1}$ | 0.155 |
| F(000) | 1328.0 |
| Crystal size/mm$^3$ | 0.1 × 0.28 × 0.49 |
| Radiation | MoKα (λ = 0.71073) |
| 2Θ range for data collection/° | 0.951 to 27.995 |
| Index ranges | −13 ≤ h ≤ 13, −15 ≤ k ≤ 15, −28 ≤ l ≤ 28 |
| Reflections collected | 38576 |
| Independent reflections | 6295 |
| Data/restraints/parameters | 415/0/6295 |
| Goodness-of-fit on F$^2$ | 1.101 |
| Final R indexes [I >= 2σ (I)] | $R_1$ = 0.0962, w$R_2$ = 0.1182 |
| Final R indexes [all data] | $R_1$ = 0.0491, w$R_2$ = 0.1630 |
| Largest diff. peak/hole/e Å$^{-3}$ | 0.258/−0.354 |

Ethyl 2-(4-chloro-2-nitrophenoxy)-2-methylpropanoate (Compound of Formula 146)

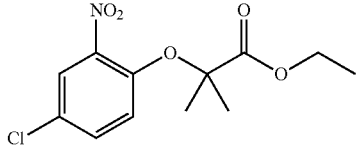 [SMILES: CCOC(=O)C(C)(C)Oc1ccc(Cl)cc1[N+](=O)[O-]]

Yield 98% (using the general procedure 1); light yellow oil; $^1$H NMR (300 MHz, Chloroform-d) δ 7.74 (d, J=2.5 Hz, 1H), 7.39 (dd, J=9.0, 2.5 Hz, 1H), 6.95 (d, J=9.0 Hz, 1H), 4.24 (q, J=7.1 Hz, 2H), 1.64 (s, 6H), 1.26 (t, J=7.1 Hz, 3H); $^{13}$C NMR (75 MHz, Chloroform-d) δ 173.22, 147.58, 143.27, 132.82, 127.16, 125.16, 121.43, 82.10, 61.94, 25.09, 14.09; IR (ATR, neat): 2988, 1735, 1604, 1531, 1478, 1384, 1354, 1281, 1176, 1100, 1019, 882, 843, 655; HRMS (ESI+) calcd (m/z) for $C_{12}H_{14}NO_5ClNa$: [M–Na$^+$] 310.0449; found 310.0453.

2-(Diethylamino)-N-(2,6-dimethyl-3-nitrophenyl)acetamide (Compound of Formula 147)

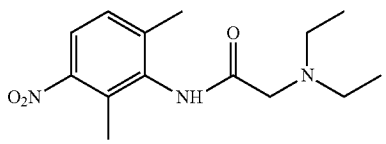 [SMILES: CCN(CC)CC(=O)Nc1c(C)ccc([N+](=O)[O-])c1C]

Yield 71% (using the general procedure 1, 19 hours); yellow oil; $^1$H NMR (400 MHz, Chloroform-d) δ 9.08 (s, 1H), 7.73 (d, J=8.4 Hz, 1H), 7.20 (d, J=8.4 Hz, 1H), 3.24 (s, 2H), 2.71 (q, J=7.1 Hz, 4H), 2.38 (s, 3H), 2.29 (s, 3H), 1.14 (t, J=7.1 Hz, 6H); $^{13}$C NMR (101 MHz, Chloroform-d) δ 170.52, 148.99, 141.23, 135.91, 130.72, 128.15, 123.01, 57.38, 48.97, 19.21, 14.87, 12.58. IR (ATR, neat): 3260, 2969, 1673, 1518, 1485, 1343, 1290, 1203, 1088, 824, 747, 503; HRMS (ESI+) calcd (m/z) for $C_{14}H_{22}N_3O_3$: [M$^+$] 280.1652; found 280.1656.

1-Cyclopropyl-4-nitrobenzene (Compound of Formula 148)

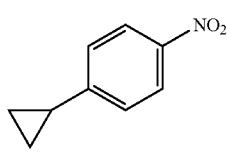 [SMILES: O=[N+]([O-])c1ccc(C2CC2)cc1]

Yield 65.7% (using the general procedure 1); light yellow oil; $^1$H NMR (300 MHz, Chloroform-d) δ 8.42-7.91 (m, 2H), 7.26-6.96 (m, 2H), 2.24-1.74 (m, 1H), 1.27-1.03 (m, 2H), 0.94-0.69 (m, 2H); $^{13}$C NMR (75 MHz, Chloroform-d) δ 152.64, 145.88, 125.97, 123.67, 15.89, 11.04.

1-Fluoro-2-nitrobenzene (Compound of Formula 149)

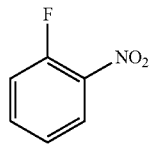

Yield 19.2% (using the general procedure 1); yellowish oil; $^1$H NMR (300 MHz, Chloroform-d) δ 8.23-8.05 (m, 1H), 7.76-7.60 (m, 1H), 7.54-7.25 (m, 2H); $^{13}$C NMR (75 MHz, Chloroform-d) δ 155.60 (d, J=264.8 Hz), 137.55, 135.63 (d, J=8.6 Hz), 126.16 (d, J=2.8 Hz), 124.61 (d, J=4.4 Hz), 118.47 (d, J=20.6 Hz); $^{19}$F NMR (282 MHz, Chloroform-d) δ −117.65.

1-(tert-Butyl)-2-nitrobenzene (Compound of Formula 150)

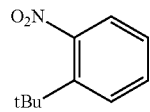

Yield 9.4% (using the general procedure 1); yellowish oil; $^1$H NMR (300 MHz, Chloroform-d) δ 7.58-7.44 (m, 1H), 7.36 (ddd, J=8.2, 6.3, 2.4 Hz, 1H), 7.30-7.12 (m, 2H), 1.34 (s, 9H); $^{13}$C NMR (75 MHz, Chloroform-d) δ 151.34, 141.30, 130.76, 128.62, 126.87, 123.91, 35.71, 30.72.

1-Methoxy-2-nitrobenzene (Compound of Formula 151)

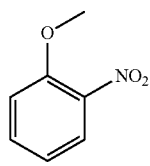

Yield 33% (using the general procedure 1); yellowish oil; $^1$H NMR (300 MHz, Chloroform-d) δ 7.83 (dd, J=8.1, 1.7 Hz, 1H), 7.54 (ddd, J=8.4, 7.4, 1.7 Hz, 1H), 7.20-6.92 (m, 2H), 3.95 (s, 3H); $^{13}$C NMR (75 MHz, Chloroform-d) δ 153.00, 134.23, 125.70, 120.31, 113.56, 56.52.

1-Methyl-2-nitrobenzene (Compound of Formula 152)

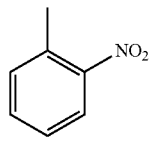

Yield 45.3% (using the general procedure 1); yellowish oil; ¹H NMR (300 MHz, Chloroform-d) δ 7.95 (d, J=8.2 Hz, 1H), 7.49 (t, J=7.4 Hz, 1H), 7.40-7.27 (m, 2H), 2.59 (s, 3H); ¹³C NMR (75 MHz, Chloroform-d) δ 149.32, 133.54, 133.01, 132.77, 126.90, 124.63, 20.39.

4-Nitro-1,1'-biphenyl (Compound of Formula 153)

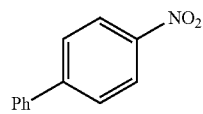

Yield 39.6% (using the general procedure 1); yellow solid; mp 113-114° C.; ¹H NMR (300 MHz, Chloroform-d) δ 8.30 (d, J=8.8 Hz, 2H), 7.74 (d, J=8.8 Hz, 2H), 7.69-7.58 (m, 2H), 7.58-7.39 (m, 3H); ¹³C NMR (75 MHz, Chloroform-d) δ 147.68, 147.15, 138.84, 129.19, 128.95, 127.84, 127.43, 124.15.

4,4,5,5-Tetramethyl-2-(2-nitrophenyl)-1,3,2-dioxaborolane (Compound of Formula 154)

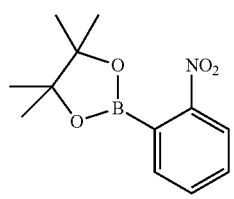 [SMILES: CC1(C)OB(c2ccccc2[N+](=O)[O-])OC1(C)C]

Yield 38.4% (using the general procedure 1); orange oil; ¹H NMR (300 MHz, Chloroform-d) δ 8.14 (d, J=8.1 Hz, 1H), 7.71-7.60 (m, 1H), 7.60-7.46 (m, 2H), 1.42 (s, 12H); ¹³C NMR (75 MHz, Chloroform-d) δ 151.01, 133.75, 132.88, 130.08, 123.00, 84.65, 24.77.

1-Nitro-2-(trifluoromethyl)benzene (Compound of Formula 155)

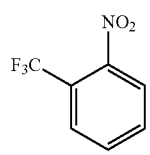 [SMILES: O=[N+]([O-])c1ccccc1C(F)(F)F]

Yield 12.2% (using the general procedure 1, 19 hours); yellow oil; yield 15% (using the general procedure 2); ¹H NMR (300 MHz, Chloroform-d) δ 7.95-7.78 (m, 2H), 7.80-7.67 (m, 2H); ¹³C NMR (75 MHz, Chloroform-d) δ 148.26, 133.14, 132.58, 127.97 (q, J=5.2 Hz), 125.00, 123.81 (q, J=33.7 Hz), 122.06 (q, J=271.5 Hz); ¹⁹F NMR (282 MHz, Chloroform-d) δ −60.01.

1-Bromo-2-nitrobenzene (Compound of Formula 156)

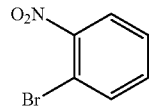

Yield 36.8% (using the general procedure 1); yellow solid; mp 42-44° C.; ¹H NMR (300 MHz, Chloroform-d) δ 7.84 (dd, J=7.5, 2.3 Hz, 1H), 7.75 (dt, J=8.3, 1.9 Hz, 1H), 7.56-7.37 (m, 2H); ¹³C NMR (75 MHz, Chloroform-d) δ 149.94, 135.12, 133.21, 128.27, 125.63, 114.51.

1-Nitro-2-(trifluoromethoxy)benzene (Compound of Formula 157)

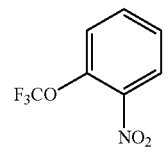

Yield 14.8% (using the general procedure 1, 19 hours); yellowish oil; yield 17.3% (using the general procedure 2, 19 hours); ¹H NMR (300 MHz, Chloroform-d) δ 7.99 (dd, J=8.4, 1.7 Hz, 1H), 7.67 (td, J=7.8, 1.7 Hz, 1H), 7.56-7.39 (m, 2H); ¹³C NMR (75 MHz, Chloroform-d) δ 142.85, 141.35 (q, J=2.0 Hz), 134.25, 127.61, 125.95, 123.26, 120.24 (q, J=260.6 Hz); ¹⁹F NMR (282 MHz, Chloroform-d) δ −57.58.

(2-Nitrophenyl)(trifluoromethyl)sulfane (Compound of Formula 158)

Yield 41% (using the general procedure 1, 19 hours); yield 44.1% (using the general procedure 2); yellowish oil; ¹H NMR (400 MHz, Chloroform-d) δ 8.12 (dd, J=8.2, 1.4 Hz, 1H), 7.84 (d, J=8.0 Hz, 1H), 7.68 (td, J=7.8, 1.4 Hz, 1H), 7.55 (td, J=7.9, 1.2 Hz, 1H); ¹³C NMR (101 MHz, Chloroform-d) δ 149.29, 133.70, 132.72-131.91 (m), 129.42, 188.66 (q, J=311.0 Hz), 125.70, 124.37-124.06 (m); ¹⁹F NMR (376 MHz, Chloroform-d) δ −41.23.

1-(4-Nitrophenyl)pyrrolidine-2,5-dione (Compound of Formula 159)

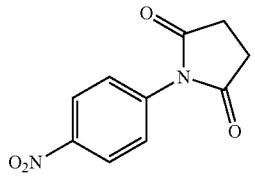 [SMILES: O=C1CCC(=O)N1c1ccc([N+](=O)[O-])cc1]

Yield 42.7% (using the general procedure 1, 19 hours); yield 46% (using the general procedure 2); yellow solid; mp 208-209° C.; $^1$H NMR (300 MHz, Chloroform-d) δ 8.41 (d, J=8.9 Hz, 2H), 7.67 (d, J=8.9 Hz, 2H), 3.03 (s, 4H); $^{13}$C NMR (75 MHz, Chloroform-d) δ 175.35, 147.16, 137.53, 127.00, 124.54, 28.56.

1-Chloro-2-nitrobenzene (Compound of Formula 160)

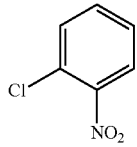

Yield 38.4% (using the general procedure 1); yellowish solid; mp 32-33° C.; $^1$H NMR (300 MHz, Chloroform-d) δ 7.87 (dd, J=8.0, 1.6 Hz, 1H), 7.63-7.47 (m, 2H), 7.42 (ddd, J=8.7, 6.9, 2.0 Hz, 1H); $^{13}$C NMR (75 MHz, Chloroform-d) δ 148.28, 133.16, 131.93, 127.60, 127.13, 125.60.

N,N-Dimethyl-2-nitroaniline (Compound of Formula 161)

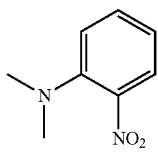

Yield 36.4% (using the general procedure 1); yellow oil; $^1$H NMR (300 MHz, Chloroform-d) δ 8.70 (d, J=2.7 Hz, 1H), 8.21 (dd, J=9.5, 2.7 Hz, 1H), 7.01 (d, J=9.4 Hz, 1H), 3.06 (s, 6H); $^{13}$C NMR (75 MHz, Chloroform-d) δ 149.16, 136.56, 135.85, 127.80, 124.22, 116.63, 42.45.

(4-Nitrophenyl)(phenyl)methanone (Compound of Formula 162)

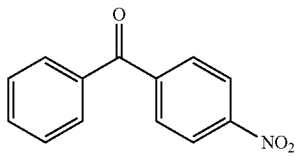 [SMILES: O=C(c1ccccc1)c1ccc([N+](=O)[O-])cc1]

Yield 24.5% (using the general procedure 1, 19 hours); light yellow solid; mp 136-139° C.; $^1$H NMR (400 MHz, Chloroform-d) δ 8.35 (d, J=8.6 Hz, 2H), 7.94 (d, J=8.6 Hz, 2H), 7.80 (d, J=8.3 Hz, 2H), 7.66 (t, J=7.4 Hz, 1H), 7.53 (t, J=7.8 Hz, 2H); $^{13}$C NMR (101 MHz, Chloroform-d) δ 194.79, 149.84, 142.89, 136.29, 133.47, 130.70, 130.10, 128.69, 123.55.

1-Chloro-2-nitro-4-(trifluoromethoxy)benzene (Compound of Formula 163)

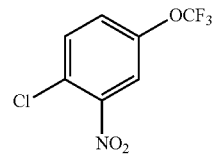

Yield 34.5% (using the general procedure 1, 19 hours); colorless oil; yield 36.4% (using the general procedure 2); $^1$H NMR (500 MHz, Chloroform-d) δ 7.78 (d, J=2.8 Hz, 1H), 7.62 (d, J=8.9 Hz, 1H), 7.41 (ddd, J=8.9, 2.9, 1.0 Hz, 1H); $^{13}$C NMR (126 MHz, Chloroform-d) δ 148.13, 147.46 (q, J=2.3 Hz), 133.23, 125.65, 125.52, 120.14 (q, J=260.3 Hz), 118.50; $^{19}$F NMR (471 MHz, Chloroform-d) δ −58.30.

Methyl 4-(tert-butyl)-2-nitrobenzoate (Compound of Formula 164)

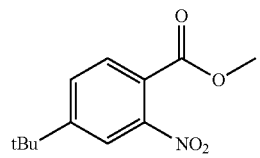 [SMILES: COC(=O)c1ccc(C(C)(C)C)cc1[N+](=O)[O-]]

Yield 24.9% (using the general procedure 1, 19 hours); light yellow oil; yield 26.8% (using the general procedure 2); $^1$H NMR (400 MHz, Chloroform-d) δ 7.86 (d, J=1.7 Hz, 1H), 7.73-7.61 (m, 2H), 3.90 (s, 3H), 1.36 (s, 9H); $^{13}$C NMR (101 MHz, Chloroform-d) δ 165.80, 156.50, 148.64, 129.83, 129.67, 124.30, 120.92, 53.11, 35.39, 30.89.

(2-Nitrophenyl)(phenyl)methanone (Compound of Formula 165)

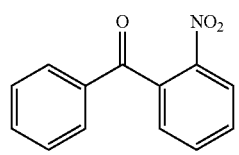 [SMILES: O=C(c1ccccc1)c1ccccc1[N+](=O)[O-]]

Yield 32.7% (using the general procedure 1, 19 hours); light yellow solid; mp 104-106° C.; $^1$H NMR (400 MHz, Chloroform-d) δ 8.24 (d, J=8.2 Hz, 1H), 7.76 (dd, J=11.4, 8.0 Hz, 3H), 7.68 (t, J=7.8 Hz, 1H), 7.59 (t, J=7.4 Hz, 1H), 7.54-7.41 (m, 3H); $^{13}$C NMR (101 MHz, Chloroform-d) δ 193.43, 146.72, 136.24, 135.92, 134.16, 133.82, 130.52, 129.24, 128.91, 128.78, 124.48.

1-Iodo-2-nitrobenzene (Compound of Formula 166)

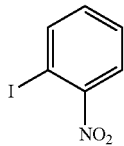

Yield 30% (using the general procedure 1); yellow oil; $^1$H NMR (300 MHz, Chloroform-d) δ 7.98 (dd, J=7.9, 1.3 Hz, 1H), 7.79 (dd, J=8.1, 1.5 Hz, 1H), 7.42 (td, J=7.8, 1.3 Hz, 1H), 7.33-7.11 (m, 1H); $^{13}$C NMR (75 MHz, Chloroform-d) δ 153.13, 141.95, 133.39, 129.08, 125.46, 86.23.

Methyl 2-nitrobenzoate (Compound of Formula 167)

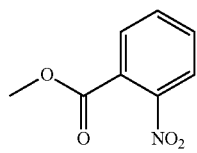

Yield 17.4% (using the general procedure 2); yellow oil; $^1$H NMR (300 MHz, Chloroform-d) δ 7.91 (dd, J=7.4, 1.9 Hz, 1H), 7.83-7.72 (m, 1H), 7.65 (pd, J=7.4, 1.7 Hz, 2H), 3.92 (s, 3H); $^{13}$C NMR (75 MHz, Chloroform-d) δ 165.89, 148.31, 132.92, 131.79, 129.90, 127.64, 123.96, 53.30.

(13S)-3-Methoxy-13-methyl-2-nitro-6,7,8,9,11,12,13,14,15,16-decahydro-17H-cyclopenta[a]phenanthren-17-one (Compound of Formula 168)

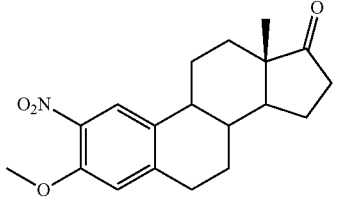 [SMILES: COc1cc2c(cc1[N+](=O)[O-])C1CC[C@]3(C)C(=O)CCC3C1CC2]

Yield 13% (using the general procedure 1); yellow solid; mp 244-248° C.; $^1$H NMR (500 MHz, Chloroform-d) δ 7.84 (s, 1H), 6.80 (s, 1H), 3.94 (s, 3H), 2.97 (p, J=11.4 Hz, 2H), 2.54 (dd, J=19.1, 8.7 Hz, 1H), 2.45-2.38 (m, 1H), 2.32-2.22 (m, 1H), 2.17 (dt, J=18.7, 8.9 Hz, 1H), 2.12-2.05 (m, 2H), 2.01 (d, J=12.3 Hz, 1H), 1.71-1.47 (m, 6H), 0.94 (s, 3H); $^{13}$C NMR (126 MHz, Chloroform-d) δ 151.16, 144.39, 137.36, 132.42, 123.12, 113.58, 56.49, 50.26, 47.87, 43.48, 37.86, 35.79, 31.33, 29.81, 26.07, 25.72, 21.54, 13.81; IR (ATR, neat): 2917, 1728, 1526, 1491, 1404, 1377, 1282, 1074, 856, 816, 657; HRMS (ESI+) calcd (m/z) for $C_{19}H_{23}NO_4$: [M−Na$^+$]352.1515; found 352.1519.

2,4-Dinitro-1-(4-(trifluoromethyl)phenoxy)benzene (Compound of Formula 169)

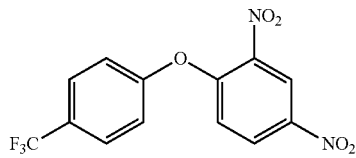 [SMILES: O=[N+]([O-])c1ccc(Oc2ccc(C(F)(F)F)cc2)c([N+](=O)[O-])c1]

Yield 5.5% (using the general procedure 1, 19 hours); white solid; mp 114-116° C. $^1$H NMR (300 MHz, Chloroform-d) δ 8.91 (d, J=2.7 Hz, 1H), 8.42 (dd, J=9.2, 2.7 Hz, 1H), 7.78 (d, J=8.5 Hz, 2H), 7.31-7.24 (m, 2H), 7.16 (d, J=9.2 Hz, 1H); $^{13}$C NMR (75 MHz, Chloroform-d) δ 156.80, 154.79, 142.59, 140.48, 129.08, 128.68 (d, J=33.2 Hz), 128.24 (q, J=3.6 Hz), 123.77 (q, J=270.7 Hz), 122.35, 120.35, 119.92; $^{19}$F NMR (282 MHz, Chloroform-d) δ −62.23; IR (ATR, neat): 3095, 1601, 1532, 1508, 1349, 1317, 1270, 1123, 1063, 833, 676, 638; HRMS (EI) calcd (m/z) for $C_{13}H_7N_2F_3O_5$: [M$^+$] 328.03016; found 328.03004.

2,6-Dihydroxy-3-nitrobenzoic acid (Compound of Formula 170)

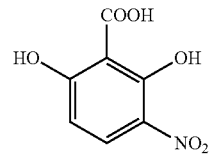

Yield 88%, 88 mg (using the general procedure I); yellow solid; mp 215.5-217.0° C.; $^1$H NMR (400 MHz, Acetone-d$_6$) δ 14.95 (s, 1H), 8.00 (d, J=9.4 Hz, 1H), 6.24 (d, J=9.4 Hz, 1H), 3.45 (bs, 2H); $^{13}$C NMR (101 MHz, Acetone-d$_6$) δ 176.8, 169.7, 162.7, 131.1, 129.4, 106.6, 104.5; IR (ATR, neat): 3436, 1718, 1595, 1450, 1249, 1145, 922, 824, 755, 590; HRMS (ESI+) calcd (m/z) for $C_7H_4NO_6$: [M−H] 198.0044; found 198.0049.

4-Chloro-3-nitrophenol [CAS: 610-78-6] (Compound of Formula 171)

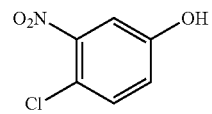

Yield 93%, 81 mg (using the general procedure I); yellow solid; mp 126° C.; $^1$H NMR (300 MHz, Chloroform-d) δ 10.47 (s, 1H), 8.11 (d, J=2.6 Hz, 1H), 7.54 (dd, J=9.0, 2.6 Hz, 1H), 7.14 (d, J=9.0 Hz, 1H); $^{13}$C NMR (75 MHz, Chloroform-d) δ 153.7, 137.6, 125.3, 124.4, 121.5.

Cyclopropyl(5-nitrothiophen-2-yl)methanone [CAS: 1330049-33-6] (Compound of Formula 172)

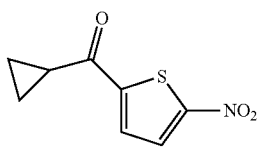 [SMILES: O=C(c1ccc([N+](=O)[O-])s1)C1CC1]

Yield 84%, 83 mg (using the general procedure I, 19 hours); white solid; mp 104-105° C.; $^1$H NMR (300 MHz, Chloroform-d) δ 8.52 (d, J=1.4 Hz, 1H), 8.29 (d, J=1.5 Hz, 1H), 2.55 (tt, J=7.7, 4.5 Hz, 1H), 1.35-1.24 (m, 2H), 1.21-1.08 (m, 2H); $^{13}$C NMR (75 MHz, Chloroform-d) δ 192.2, 145.4, 132.9, 125.1, 17.9, 12.4.

Phenytoin-NO$_2$ (Compound of Formula 173)

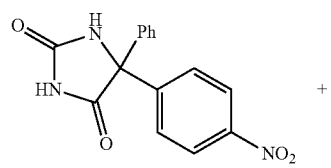

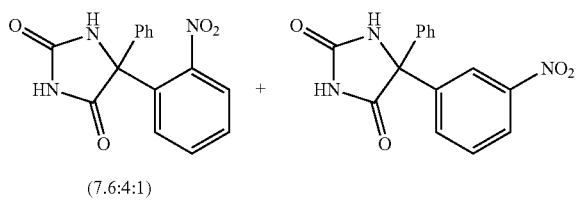

(7.6:4:1)

Total yield of isomers 98%, 145.5 mg (using the general procedure 1); white solid; mp 235-240° C.; $^1$H NMR of left molecule (500 MHz, DMSO-d$_6$) δ 11.3 (s, 1H), 9.51 (s, 1H), 8.29 (d, J=10.0 Hz, 2H), 7.67 (d, J=10.0 Hz, 2H); 7.43-7.34 (m, 5H); $^1$H NMR of middle molecule (500 MHz, DMSO-d$_6$) δ 11.3 (s, 1H), 9.5 (s, 1H), 8.30-8.24 (m, 2H), 7.88 (d, J=10.0 Hz, 1H), 7.74 (t, 10.0 Hz, 1H), 7.43-7.34 (m, 5H), $^1$H NMR of right molecule (500 MHz, DMSO-d$_6$) δ 11.1 (s, 1H), 9.3 (s, 1H), 8.11 (d, J=5.0 Hz, 1H), 7.97 (t, J=5.0 Hz, 1H), 7.98-7.91 (m, J=5.0 Hz, 3H), 7.43-7.34 (m, 5H). $^{13}$C NMR of mixture (125 MHz, Chloroform-d) δ 175.3, 174.57, 174.41, 156.44, 156.27, 148.2, 147.6, 147.0, 142.0, 140.4, 135.55, 134.89, 133.8, 130.8, 129.3, 129.2, 128.95, 128.93, 129.91, 128.52, 128.47, 127.0, 126.9, 125.1, 123.2, 123.7, 121.5, 121.4, 70.6, 70.5, 70.1; IR (ATR, neat): 3048, 1771, 1714, 1519, 1347, 1225, 1095, 852, 691; HRMS (ESI+) calcd (m/z) for C$_{15}$H$_{11}$N$_3$O$_4$Na: [M+Na$^+$] 320.0642; found 320.0642.

Nimesulide-NO$_2$ (Compound of Formula 174)

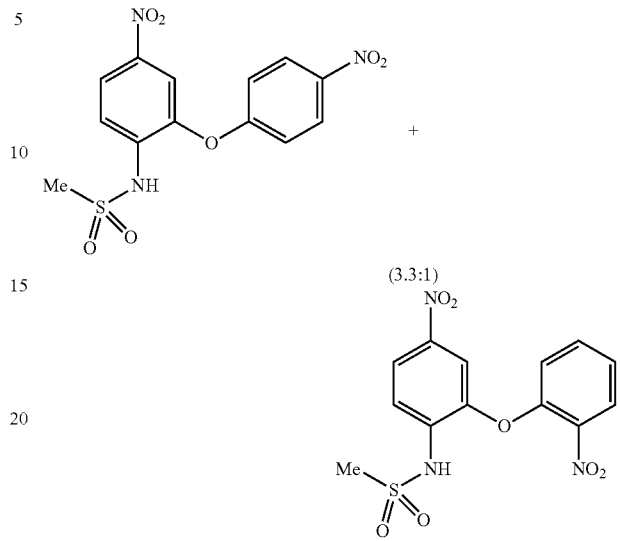

(3.3:1)

Yield of left molecule 76.1%, 134 mg (using the general procedure I); yellow solid, mp 177.2-178.0° C.; $^1$H NMR (400 MHz, Chloroform-d) δ 10.36 (s, 1H), 8.54-8.24 (m, 2H), 8.18 (dd, J=9.1, 2.6 Hz, 1H), 7.96 (d, J=2.6 Hz, 1H), 7.82 (d, J=9.1 Hz, 1H), 7.26 (d, J=9.2 Hz, 2H), 3.18 (s, 3H); $^{13}$C NMR (101 MHz, Chloroform-d) δ 166.67, 149.31, 148.33, 148.26, 142.28, 131.20, 126.79, 123.33, 121.74, 46.12; IR (ATR, neat): 3264, 1717, 1586, 1509, 1336, 1226, 1160, 965, 897, 744, 514; HRMS (ESI+) calcd (m/z) for C$_{13}$H$_1$N$_3$NaO$_7$S: [M+Na] 376.0212; found 376.0214.

Yield of right molecule 23%, 40.5 mg (using the general procedure 1); yellow-red solid, mp 173.1-173.6° C.; $^1$H NMR (300 MHz, Chloroform-d) δ 8.16 (dd, J=8.2, 1.6 Hz, 1H), 8.06 (dd, J=9.0, 2.4 Hz, 1H), 7.85 (d, J=9.0 Hz, 1H), 7.77 (td, J=8.2, 1.6 Hz, 1H), 7.60 (s, 1H), 7.57 (d, J=2.4 Hz, 1H), 7.56-7.46 (m, 1H), 7.33 (dd, J=8.2, 1.1 Hz, 1H), 3.19 (s, 3H); $^{13}$C NMR (75 MHz, Chloroform-d) δ 147.1, 145.5, 143.6, 141.3, 135.7, 134.3, 127.1, 126.9, 123.4, 120.5, 117.9, 111.1, 40.5; IR (ATR, neat): 3263, 1599, 1517, 1336, 1267, 1186, 1160, 952, 738, 516; HRMS (ESI+) calcd (m/z) for C$_{13}$H$_{11}$N$_3$NaO$_7$S: [M+Na] 376.0212; found 376.0212.

Secinidazole [CAS: 3366-95-8] (Compound of Formula 175)

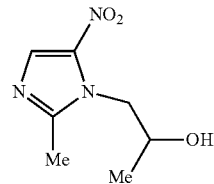 [SMILES: Cc1ncc([N+](=O)[O-])n1CC(C)O]

Yield 44%, 41 mg (using the general procedure II, 19 hours); white solid, mp 80.5-81.5° C.; $^1$H NMR (300 MHz, Acetonitrile-d$_3$) δ 7.91 (s, 1H), 4.60-4.21 (m, 1H), 4.21-3.90 (m, 2H), 3.26 (s, 1H), 2.46 (s, 3H), 1.23 (d, J=5.9 Hz, 3H); $^{13}$C NMR (101 MHz, Acetonitrile-d$_3$) δ 151.6, 138.6, 132.3, 66.0, 52.4, 19.7, 13.7; IR (ATR, neat): 3503, 3136, 1526,

Ethyl 1-(4-nitrophenyl)-3-(trifluoromethyl)-1H-pyrazole-4-carboxylate and ethyl 1-(2-nitrophenyl)-3-(trifluoromethyl)-1H-pyrazole-4-carboxylate (Compound of Formula 176)

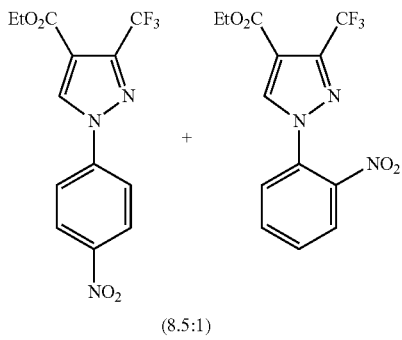 [SMILES: CCOC(=O)c1cn(-c2ccc([N+](=O)[O-])cc2)nc1C(F)(F)F ; CCOC(=O)c1cn(-c2ccccc2[N+](=O)[O-])nc1C(F)(F)F]

(8.5:1)

Yield of left molecule 83%, 136.5 mg (using the general procedure II); yellow solid; mp 115.3-116.5° C.; $^1$H NMR (400 MHz, Chloroform-d) δ 8.41 (d, J=9.0 Hz, 2H), 7.75-7.59 (m, 2H), 4.41 (q, J=7.1 Hz, 2H), 1.41 (t, J=7.1 Hz, 3H); $^{13}$C NMR (101 MHz, Chloroform-d) δ 160.5, 148.2, 143.9, 143.3, 132.74 (q, J=40.5 Hz), 126.8, 124.6, 118.95 (q, J=271.7 Hz), 117.9 (q, J=1.1 Hz), 61.6, 14.1; $^{19}$F NMR (376 MHz, Chloroform-d) δ −54.94; IR (ATR, neat): 1735, 1523, 1345, 1224, 1151, 1018, 970, 855, 756, 704; HRMS (ESI+) calcd (m/z) for $C_{13}H_{11}F_3N_3O_4$: [M+H] 330.0696; found 330.0697.

Yield of right molecule 10%, 16.5 mg (using the general procedure II); yellow solid; mp 119-120° C.; $^1$H NMR (400 MHz, Chloroform-d) δ 8.23 (dd, J=8.0, 1.7 Hz, 1H), 8.20-8.15 (m, 1H), 7.88-7.71 (m, 2H), 7.56 (dd, J=7.7, 1.6 Hz, 1H), 4.41 (q, J=7.1 Hz, 2H), 1.41 (t, J=7.1 Hz, 3H); $^{13}$C NMR (101 MHz, Chloroform-d) δ 160.5 (q, J=1.0 Hz), 144.9, 143.5, 134.3 (q, J=40.3 Hz), 133.9, 132.9, 131.4, 129.7 (q, J=1.0 Hz), 125.7, 118.9 (q, J=271.6 Hz), 116.9 (q, J=1.5 Hz), 61.4, 14.1; $^{19}$F NMR (376 MHz, Chloroform-d) δ −56.66; IR (ATR, neat): 2914, 1724, 1565, 1385, 1249, 1145, 1067, 972, 752; HRMS (ESI+) calcd (m/z) for $C_{13}H_{10}F_3N_3O_4Na$: [M+Na]352.0516; found 352.0515.

Procymidone-NO$_2$ (Compound of Formula 177)

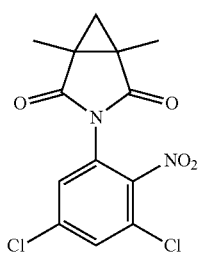 [SMILES: CC12CC1(C)C(=O)N(c1cc(Cl)cc(Cl)c1[N+](=O)[O-])C2=O]

Yield 91%, 150 mg (using the general procedure I, 19 hours); yellow solid; mp 199.3-200.0° C.; $^1$H NMR (400 MHz, Chloroform-d) δ 7.58 (d, J=2.1 Hz, 1H), 7.33 (s, 1H), 1.91 (d, J=4.8 Hz, 1H), 1.48 (s, 6H), 1.22 (d, J=4.8 Hz, 1H); $^{13}$C NMR (101 MHz, Chloroform-d) δ 174.7, 144.5, 137.5, 131.1, 129.0, 128.4, 127.1, 32.6, 30.7, 9.9; IR (ATR, neat): 3074, 1780, 1720, 1571, 1442, 1360, 1143, 1143, 1110, 806, 731, 522; HRMS (ESI+) calcd (m/z) for $C_{13}H_{10}F_3N_3O_4Na$: [M+H] 329.009; found 329.0089.

Arbutin Peracetate-NO$_2$ (Compound of Formula 178)

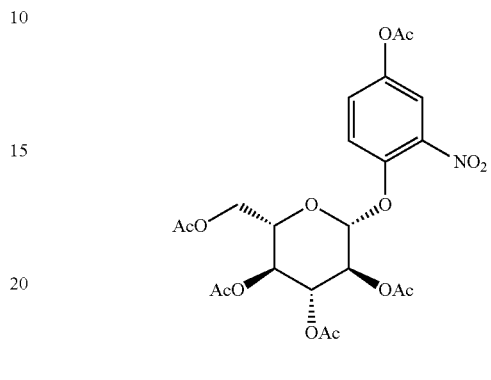

Yield 74%, 195 mg (using the general procedure II); yellow solid, mp 149.6-150.0° C.; $^1$H NMR (300 MHz, Acetonitrile-d$_3$) δ 7.63 (d, J=2.7 Hz, 1H), 7.52-7.34 (m, 2H), 5.42-5.31 (m, 2H), 5.30-5.11 (m, 2H), 4.24 (qd, J=12.4, 3.9 Hz, 2H), 4.15-4.02 (m, 1H), 2.29 (d, J=3.3 Hz, 3H), 2.09-1.93 (m, 15H); $^{13}$C NMR (75 MHz, Acetonitrile-d$_3$) δ 169.9, 169.5, 169.2, 168.9, 168.9, 146.4, 145.2, 140.4, 127.3, 119.2, 118.2, 99.2, 71.8, 71.6, 69.9, 67.6, 61.2, 19.8, 19.6, 19.6, 19.5, 19.5; IR (ATR, neat): 1751, 1533, 1366, 1227, 1185, 1038, 926, 597; HRMS (ESI+) calcd (m/z) for $C_{22}H_{25}KNO_{14}$: [M+K] 566.0907; found 566.0898.

Nordihydrocapsaicin-NO$_2$ (Compound of Formula 179)

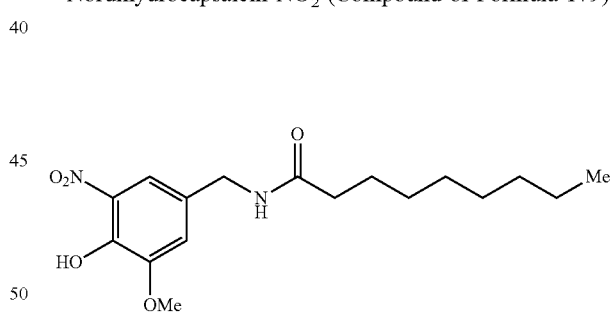

Yield 94%, 159 mg (using the general procedure I); yellow solid; mp 121.5-122.5° C.; $^1$H NMR (400 MHz, Chloroform-d) δ 10.72 (s, 1H), 7.57 (d, J=1.9 Hz, 1H), 7.12 (d, J=1.9 Hz, 1H), 5.99 (s, 1H), 4.41 (d, J=6.0 Hz, 2H), 3.94 (s, 3H), 2.26 (t, J=7.6 Hz, 2H), 1.67 (p, J=7.4 Hz, 2H), 1.39-1.21 (m, 11H), 0.88 (t, J=6.8 Hz, 3H); $^{13}$C NMR (101 MHz, Chloroform-d) δ 173.3, 150.2, 145.7, 133.4, 130.2, 117.5, 114.2, 56.7, 42.7, 36.7, 31.8, 29.3, 29.1, 25.7, 22.6, 14.1; IR (ATR, neat): 3296, 2920, 2847, 1642, 1532, 1327, 1268, 1220, 1130, 1060, 857, 689; HRMS (ESI+) calcd (m/z) for $C_{17}H_{30}N_3O_5$: [M+NH$_4$] 356.2180; found 356.2186.

N-Boc-p-nitro-L-phenylalanine [CAS: 33305-77-0] and N-Boc-o-nitro-L-phenylalanine [CAS: 185146-84-3] (Compound of Formula 180)

with a compound of formula (I)

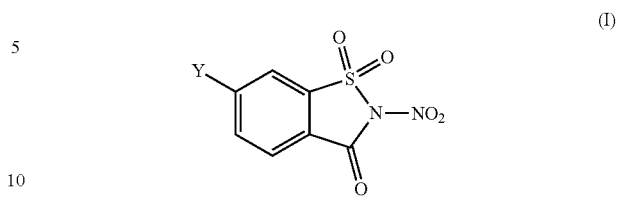

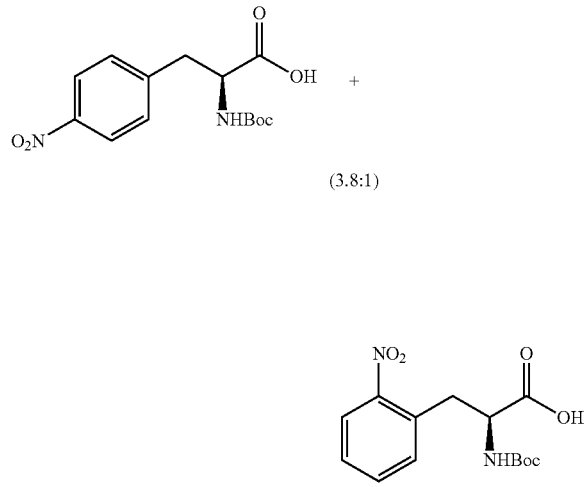 [SMILES: CC(C)(C)OC(=O)N[C@@H](Cc1ccc([N+](=O)[O-])cc1)C(=O)O ; CC(C)(C)OC(=O)N[C@@H](Cc1ccccc1[N+](=O)[O-])C(=O)O]

(3.8:1)

wherein Y is selected from the group consisting of hydrogen and nitro.

2. The process according to claim 1, wherein compound (A) includes at least one acid-sensitive residue.

3. The process according to claim 1, wherein the aromatic ring or the heteroaromatic ring of compound (A) includes at least one electron donating group as residue.

4. The process according to claim 1, wherein the aromatic ring or the heteroaromatic ring of compound A includes at least one electron withdrawing group as residue.

5. The process according to claim 1, wherein the compound (A) includes or is a 5- or 6-membered aromatic or heteroaromatic ring optionally substituted by one or more organic residues R, wherein the organic residue R is selected from the group consisting of fluoro, chloro, bromo, iodo, amino, cyano, hydroxy, nitro, $C_{1-12}$ alkyl, $C_{2-15}$ alkenyl, $C_{2-15}$ alkynyl, $C_{3-15}$ cycloalkyl, $C_{3-15}$ cycloalkenyl, cycloalkynyl, $C_{3-5}$ alkylene, $C_{3-5}$ cycloalkylene, $C_{3-5}$ alkenylene, $C_{3-5}$ alkynylene, halo-$C_{1-6}$ alkyl, hydroxy-$C_{1-6}$ alkyl, halo-$C_{3-15}$ cycloalkyl, $C_{1-10}$ alkoxy, $C_{3-5}$ cycloalkoxy, alkylenedioxy, $C_{1-6}$ acyl, $C_{3-6}$ cycloacyl, $C_{1-6}$ acyloxy, $C_{3-6}$ cycloacyloxy, arylalkyl, heteroarylalkyl, aryl, and heteroaryl group, and where the organic residue R may optionally form an annealed ring system with other rings selected from cycloalkyl, aryl, and heteroaryl rings.

Yield of left molecule 51%, 125 mg (using the general procedure 1), yellow solid; mp 111.9-112.6° C.; $^{1}$H NMR (300 MHz, DMSO-$d_6$) δ 12.71 (s, 1H), 8.15 (d, J=8.6 Hz, 2H), 7.53 (d, J=8.4 Hz, 2H), 7.20 (d, J=8.6 Hz, 1H), 4.19 (ddd, J=10.5, 8.5, 4.5 Hz, 1H), 3.18 (dd, J=13.7, 4.6 Hz, 1H), 2.96 (dd, J=13.7, 10.5 Hz, 1H), 1.30 (s, 9H); $^{13}$C NMR (75 MHz, DMSO-$d_6$) δ 173.0, 155.3, 146.4, 146.2, 130.4, 123.1, 78.1, 54.5, 36.2, 28.0.

Yield of right molecule 13%, 20 mg (using the general procedure 1), yellow solid, mp 129-131° C.; $^{1}$H NMR (300 MHz, DMSO-$d_6$) δ 12.36 (s, 1H), 7.91 (d, J=8.1 Hz, 1H), 7.72 (dt, J=13.8, 6.9 Hz, 3H), 7.50 (t, J=7.5 Hz, 1H), 5.33 (q, J=8.3 Hz, 1H), 2.91-2.54 (m, 2H), 1.31 (s, 9H); $^{13}$C NMR (75 MHz, DMSO-$d_6$) δ 171.2, 154.7, 147.9, 138.3, 128.2, 128.2, 123.9, 78.2, 46.9, 28.1.

6. The process according to claim 1, wherein the compound (A) includes or is a fused aromatic or heteroaromatic ring system having 2 to 5 aromatic or heteroaromatic rings which may be optionally substituted by one or more organic residues R, wherein the organic residue R is selected from the group consisting of fluoro, chloro, bromo, iodo, amino, cyano, hydroxy, nitro $C_{1-12}$ alkyl, $C_{2-15}$ alkenyl, $C_{2-15}$ alkynyl, $C_{3-15}$ cycloalkyl, $C_{3-15}$ cycloalkenyl, cycloalkynyl, $C_{3-5}$ alkylene, $C_{3-5}$ cycloalkylene, $C_{3-5}$ alkenylene, $C_{3-5}$ alkynylene, halo-$C_{1-6}$ alkyl, hydroxy-$C_{1-6}$ alkyl, halo-$C_{3-15}$ cycloalkyl, $C_{1-10}$ alkoxy, $C_{3-5}$ cycloalkoxy, alkylenedioxy, $C_{1-6}$ acyl, $C_{3-6}$ cycloacyl, $C_{1-6}$ acyloxy, $C_{3-6}$ cycloacyloxy, arylalkyl, heteroarylalkyl, aryl, and heteroaryl group, and where the organic residue R may optionally form an annealed ring system with other rings selected from cycloalkyl, aryl, and heteroaryl rings.

The invention claimed is:

1. A process for preparing a nitrated compound, comprising the step of reacting a compound (A) having at least one aromatic or heteroaromatic ring optionally substituted by one or more organic residues R, wherein the organic residue R is selected from the group consisting of fluoro, chloro, bromo, iodo, amino, cyano, hydroxy, nitro, $C_{1-12}$ alkyl, $C_{2-15}$ alkenyl, $C_{2-15}$ alkynyl, $C_{3-15}$ cycloalkyl, $C_{3-15}$ cycloalkenyl, cycloalkynyl, $C_{3-5}$ alkylene, $C_{3-5}$ cycloalkylene, $C_{3-5}$ alkenylene, $C_{3-5}$ alkynylene, halo-$C_{1-6}$ alkyl, hydroxy-$C_{1-6}$ alkyl, halo-$C_{3-15}$ cycloalkyl, $C_{1-10}$ alkoxy, $C_{3-5}$ cycloalkoxy, alkylenedioxy, $C_{1-6}$ acyl, $C_{3-6}$ cycloacyl, $C_{1-6}$ acyloxy, $C_{3-6}$ cycloacyloxy, arylalkyl, heteroarylalkyl, aryl, and heteroaryl group, and where the organic residue R may optionally form an annealed ring system with other rings selected from cycloalkyl, aryl, and heteroaryl rings, and wherein the heteroaromatic ring includes at least one heteroatom selected from the group consisting of oxygen, sulfur, phosphor, selenium and nitrogen, 7. The process according to claim 1, wherein the heteroaromatic ring or ring system is selected from the group consisting of pyrrole, thiophene, furan, imidazole, thiazole, pyrimidine, pyridine, pyrazine, pyridazine, isoxazole, oxazole, indole, isoindole, indolizine, quinoline, isoquinoline, purine, carbazole, dibenzofuran, acridine, purine, guanine, xanthine, uric acid, benzothiophen, benzofuran, dibenzothiophen, thianthren, xanthen, phenoxatiin, isochinoline, phthalazine, 1,8-naphthydrine, quinazoline, quinoxaline, cinnoline, pteridine, perimidine, 1,7-phenanthroline, phenazine, phosphindole, phthalimide, furazan and phosphinoline.

8. The process according to claim 1, wherein the aromatic ring or ring system is selected from the group consisting of benzene, pentalene, indene, indan, naphthalene, 1,1'-binaphthalene, azulene, heptalene, biphenylene, as-indacene, s-indacene, acenaphthylene, fluorene phenalene, phenanthrene, anthracene, fluoranthene acephenanthrylene, aceanthrylenetriphenylene, pyrene chrysene, naphthacene, pleiadene, picene and perylene.

9. The process according to claim 1, wherein the compound of formula (I) is the compound of formula (Ia)

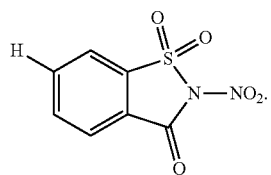

(Ia)

10. The process according to claim 1, wherein the compound of formula (I) is the compound of formula (Ib)

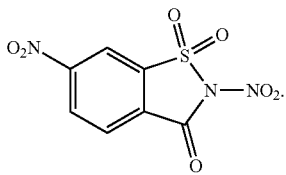

(Ib)

11. The process according to claim 1, wherein the reaction is carried out in a solvent selected from the group consisting of hexafluoroisopropanol, acetonitrile, nitromethane, methylenechloride, trifluoroethanol, tetrahydrofuran, hexane, benzene, toluene, and mixtures thereof.

12. The process according to claim 1, wherein the reaction is carried out in the presence of a catalyst selected from the group consisting of acetic acid, trimethylacetic acid, trichloroacetic acid, trifluoroacetic acid, benzoic acid, iron (II) triflate, iron (III) triflate, magnesium (II) triflate, zinc (II) triflate, cupper (II) triflate, iron (II) bromide, iron (III) bromide, magnesium perchlorate, and mixtures thereof.

13. The process according to claim 12, wherein the catalyst is selected from the group consisting of acetic acid, trimethylacetic acid, trichloroacetic acid, trifluoroacetic acid, benzoic acid, and mixtures thereof.

14. The process according to claim 12, wherein the catalyst is selected from the group consisting of iron (II) triflate, iron Me triflate, magnesium (II) triflate, zinc (II) triflate, cupper (II) triflate, iron (II) bromide, iron (III) bromide and magnesium perchlorate.

15. A method comprising applying a compound of formula (I)

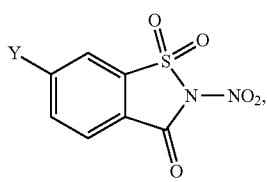

(I)

wherein Y is selected from the group consisting of hydrogen and nitro,
as nitrating agent of a compound (A) comprising an aromatic or heteroaromatic ring.

16. The process according to claim 2, wherein the acid-sensitive residue is selected from the group consisting of difluoromethoxy, trifluoromethoxy, difluoromethylthio, trifluoromethylthio, chloro, iodo, methoxy, ethoxy, propoxy, butoxy, amino, methylamino, dimethylamino, formyl, methoxycarbonyl, ethoxycarbonyl, tert-butoxycarbonyl, acyl chlorides, acid anhydrides, carboxylate esters, sulfonate esters, alkyl esters, carboxy, ketals, acetals, hydrazones carboxy, and 4,4,5,5-tetramethyl-1,3,2-dioxaborolanyl.

17. The process according to claim 3, wherein the electron donating group is selected from the group consisting of amino, carbamoyl, alkylaminocarbonyl, carboxamido, mercapto, alkylthio, hydroxy, alkoxy, alkyl, acyloxy, aryl, heteroaryl, alkenyl, and alkynyl.

18. The process according to claim 4, wherein the electron withdrawing group is selected from the group consisting of fluoro, chloro, bromo, iodo, acyl, carboxy, benzoyl, carbonyl, aldehyde, arylsulfonyl, haloalkyl, cyano, and 2,5-dioxopyrrolidinyl.

* * * * *